(12) United States Patent
Macoviak et al.

(10) Patent No.: US 7,291,168 B2
(45) Date of Patent: Nov. 6, 2007

(54) METHODS AND DEVICES FOR HEART VALVE TREATMENTS

(75) Inventors: John A. Macoviak, La Jolla, CA (US); Robert T. Chang, Belmont, CA (US); Timothy R. Machold, Moss Beach, CA (US); David A. Rahdert, San Francisco, CA (US); Rick A. Soss, Burlingame, CA (US)

(73) Assignee: Ample Medical, Inc., Foster City, CA (US)

( * ) Notice: Subject to any disclaimer, the term of this patent is extended or adjusted under 35 U.S.C. 154(b) by 209 days.

(21) Appl. No.: 10/695,433

(22) Filed: Oct. 28, 2003

(65) Prior Publication Data

US 2004/0138745 A1 Jul. 15, 2004

Related U.S. Application Data

(63) Continuation of application No. PCT/US02/31376, filed on Oct. 1, 2002.

(60) Provisional application No. 60/326,590, filed on Oct. 1, 2001.

(51) Int. Cl.
*A61F 2/06* (2006.01)
(52) U.S. Cl. ..................... 623/2.36; 623/904
(58) Field of Classification Search ...... 623/2.36–2.38; 606/151
See application file for complete search history.

(56) References Cited

U.S. PATENT DOCUMENTS

| | | |
|---|---|---|
| 4,056,854 A | 11/1977 | Boretos et al. |
| 4,994,069 A | 2/1991 | Ritchart et al. |
| 5,360,444 A | 11/1994 | Kusuhara |
| 5,370,685 A | 12/1994 | Stevens |
| 5,545,241 A | 8/1996 | Vanderauwera et al. |
| 5,776,189 A | 7/1998 | Khalid |
| 5,830,224 A | 11/1998 | Cohn et al. |
| 5,855,601 A | 1/1999 | Bessler et al. |
| 5,961,440 A | 10/1999 | Schweich, Jr. et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,099,542 A | 8/2000 | Cohn et al. |
| 6,102,932 A | 8/2000 | Kurz |
| 6,162,168 A | 12/2000 | Schweich, Jr. et al. |
| 6,165,119 A | 12/2000 | Schweich, Jr. et al. |
| 6,183,411 B1 | 2/2001 | Mortier et al. |

(Continued)

OTHER PUBLICATIONS

Wilson, W.C., "Studies in Experimental Mitral Obstruction in Relation to the Surgical Treatment of Mitral Stenosis." The British Journal of Surgery, vol. XVIII, No. 70 ;259-74.

(Continued)

*Primary Examiner*—Suzette Gherbi
(74) *Attorney, Agent, or Firm*—Ryan Kromholz and Manion, S.C.

(57) ABSTRACT

The present invention is a group of medical devices designed to improve heart valve function. The medical devices may be used individually, or in combination to supplement damaged valves, replace damaged valves, or improve damaged valves function. The medical devices include leaflet retainers, a neo-annulus, neo-leaflet, and a framework. In addition, the present invention is novel methods for surgically treating heart valves.

5 Claims, 30 Drawing Sheets

U.S. PATENT DOCUMENTS

| | | | |
|---|---|---|---|
| 6,210,432 B1 | 4/2001 | Solem et al. | |
| 6,260,552 B1 | 7/2001 | Mortier et al. | |
| 6,261,222 B1 | 7/2001 | Schweich, Jr. et al. | |
| 6,312,464 B1 | 11/2001 | Navia | |
| 6,332,864 B1 | 12/2001 | Schweich, Jr. et al. | |
| 6,332,893 B1 | 12/2001 | Mortier et al. | |
| 6,338,735 B1 | 1/2002 | Stevens | |
| 6,338,740 B1 | 1/2002 | Carpentier | |
| 6,402,781 B1 | 6/2002 | Langberg et al. | |
| 6,419,695 B1 | 7/2002 | Gabbay | |
| 6,440,164 B1 | 8/2002 | DiMatteo et al. | |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,629,534 B1 * | 10/2003 | St. Goar et al. | 128/898 |
| 6,656,221 B2 | 12/2003 | Taylor et al. | |
| 6,669,709 B1 | 12/2003 | Cohn et al. | |
| 6,702,826 B2 * | 3/2004 | Liddicoat et al. | 606/151 |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 6,913,608 B2 * | 7/2005 | Liddicoat et al. | 606/151 |
| 6,945,978 B1 * | 9/2005 | Hyde | 606/142 |
| 7,004,176 B2 * | 2/2006 | Lau | 128/898 |
| 2002/0032481 A1 | 3/2002 | Gabbay | |
| 2002/0065554 A1 | 5/2002 | Streeter | |
| 2002/0129820 A1 | 9/2002 | Ryan et al. | |
| 2003/0040792 A1 | 2/2003 | Gabbay | |
| 2003/0120340 A1 | 6/2003 | Liska et al. | |
| 2003/0233022 A1 | 12/2003 | Vidlund et al. | |
| 2004/0148019 A1 | 7/2004 | Vidlund et al. | |
| 2006/0241745 A1 * | 10/2006 | Solem | 623/2.18 |

OTHER PUBLICATIONS

Bailey, et al. "Surgical Repair of Mitral Insufficiency." Diseases of the Chest, vol. XIX, No. 2, Feb. 1951, 125-137.

Henderson, et al., "The Surgical Treatment of Mitral Insufficiency. Experimental Use of Trans-planted Pericardium in Dogs." Surgery 33(6):858-868; 1953.

Sakakibara, "A Surgical Approach to the Correction of Mitral Insufficiency." Annals of Surgery. vol. 142, No. 2, Aug. 1955, 196-203.

Harken et al. "The Surgical Correction of Mitral Insufficiency." The Journal of Thoracic Surgery. 28(6):604-627., 1954.

Bailey et al. "The Surgical Correction of Mitral Insufficiency by the Use of Pericardial Grafts." The Journal of Thoracic Surgery, vol. 28, No. 6, Dec. 1954, 551-603.

Kay et al. "Surgical Treatment of Mitral Insufficiency." Surgery. vol. 37, No. 5. May 1955, 697-706.

Templeton III, et al. "Experimental Reconstruction of Cardiac Valves by Venous and Pericardial Grafts." Annals of Surgery vol. 129, No. 2, Feb. 1949, 161-176.

Moore et al. "Unsuitability of Transventricular Autogenous Slings For Diminishing Valvular Insufficiency." Surgery, vol. 33, No. 2, Feb. 1953, 173-182.

Murray et al. "Reconstruction of the Valves of the Heart." The Canadian Medical Association Journal, vol. 38, No. 4, Apr. 1938, 317-319.

Bolling et al. "Early Outcome of Mitral Valve Reconstruction in Patients With End-Stage Cardiomyopathy." J Thorac Cardiovasc Surg 1995; 109:676-683.

Kameda et al. "Annuloplasty For Severe Mitral Regurgitation Due to Dilated Cardiomyopathy." Ann Thorac Surg 1996; 61:1829-1832.

Bolling et al. "Intermediate-Term Outcome of Mitral Reconstruction in Cardiomyopathy." Journal of Thoracic Cardiovascular Surgery, vol. 115, No. 2, Feb. 1998, 381-388.

Harlan et al. Manual of Cardiac Surgery, vol. 2, 1981 Figs. 16.3-16.4.

Edmunds, Jr. et al. "Septal Defect." Atlas of Cardiothoracic Surgery 1990.

Koniaris, MD et al. "Dynamic Retention: A Technique for Closure of the Complex Abdomen in Critically III Patients." Archives of Surgery, vol. 136, No. 12, Dec. 2001, 1359-1362.

Fucci et al. "Improved Results With Mitral Valve Repair Using New Surgical Techniques." European Journal of Cardio-Thoracic Surgery, vol. 9, 1995, 621-626.

Davila et al. "Circumferential Suture of the Mitral Ring: A Method For The Surgical Correction of Mitral Insufficiency." Journal of Thoracic Surgery Nov. 1955; 30(5): 531-60.

Harken et al. "The Surgical Correction of Mitral Insufficiency" Journal of Thoracic Surgery. Dec. 1954; 28(6):604-24.

Kuykendall et al. "Surgical Correction of Chronic Mitral Insufficiency in Dogs." Surgery. Oct. 1958; 44(4):718-25.

Harken et al. "The Surgical Correction of Mitral Insufficiency." Surgical Forum 4:4-7 1953.

Davila et al. "A Method For The Surgical Correction of Mitral Insufficiency." Surgery, Gynecology and Obstetrics Apr. 1954; 98(4):407-12.

Davila et al. "The Clinical and Physiologic Criteria For Surgical Correction of Mitral Insufficiency." Journal of Thoracic Surgery Feb. 1958; 35(2):206-31.

Glover et al. "The Treatment of Mitral Insufficiency by the Purse-String Technique." Journal of Thoracic Surgery Jan. 1957; 33(1): 75-101.

Rankin et al. "A Clinical Comparison of Mitral Valve Repair Versus Valve Replacement in Ischemic Mitral Regurgitation." J Thorac Cardiovasc Surg. Feb. 1988; 95(2):165-77.

Barnard et al. "A Surgical Approach to Mitral Insufficiency." Br J Surg. May 1961; 48:655-62.

McKenzie et al. "Current Concepts in Surgical Correction of Acquired Mitral Insufficiency." Circulation. Oct. 1963; 28:603-16.

Saab et al. "Left Ventricular Aneurysm: A New Surgical Approach." Thorac Cardiovasc Surg. Feb. 1989; 37(1):11-9.

Cicek et al. "Left Ventricular Endoaneurysmorrhaphy: Effect on Left Ventricular Size, Shape and Function." Cardiology, Jul.-Aug. 1997; 88(4):340-5.

Liedtke et al. "Functional Reductions in Left Ventricular Volume." J Thorac Cardiovasc Surg. Feb. 1976; 71(2):195-206.

Sosa et al. "Recurrent Ventricular Tachycardia Associated With Postinfarction Aneurysm. Results of Left Ventricular Reconstruction." J Thorac Cardiovasc Surg. May 1992; 103(5): 855-60.

Cooley, "Repair of Postinfarction Ventricular Septal Defect." J Card Surg. Jul. 1994; 9(4):427-9.

Jatene, "Left Ventricular Aneurysmectomy. Resection or Reconstruction." J Thorqc Cardiovasc Surg 1985; 89:321-31.

de Silva et al. "Postinfarction Ventricular Septal Defect. An Efficacious Technique for Early Surgical Repair." J Throac Cardiovasc Surg. Jan. 1989; 97(1):86-9.

Tashiro et al. "Extended Endocardial Repair of Postinfarction Ventricular Septal Rupture: New Operative Technique-Modification of the Komeda-David Operation." J Card Surg. Mar. 1994; 9(2):97-102.

Daggett, "Surgical Technique for Early Repair of Posterior Ventricular Septal Rupture." J Thorac Cardiovasc Surg. Aug. 1982;84(2):306-12.

Daggett et al. "Surgery for Post-Myorcardial Infarct Ventricular Septal Defect." Ann Surg. Sep. 1977;186(3):260-71.

Dor, "Left Ventricular Aneurysms: the Endoventricular Circular Patch Plasty." Semin Thorac Cardiovasc Surg. Apr. 1997;9(2):123-30.

Antunes, "Submitral Left Ventricular Aneurysms. Correction by a New Transatrial Approach." J Thorac Cardiovasc Surg. Aug. 1987;94(2):241-5.

Alvarez et al. "Technical Improvements in the Repair of Acute Postinfarction Ventricular Septal Rupture." J Card Surg. Sep. 1992;7(3):198-202.

Cox, "Surgical Management of Left Ventricular Aneurysms: A Clarification of the Similarities and Differences Between the Jatene and Dor Techniques." Semin Thorqc Cardiovasc Surg. Apr. 1997;9(2):131-8.

Skillington et al. "Surgical Treatment for Infarct-Related Ventricular Septal Defects. Improved Early Results Combined with Analysis of Late Functional Status." J thorac Cardiovasc Surg. May 1990;99(5):798-808.

Salati et al. "Severe Diastolic Dysfunction After Endoventriculoplasty." J Thorac Cardiovasc Surg. Apr. 1995;109(4):694-701.

Yacoub et al. "Anatomic Correction of the Syndrome of Prolapsing Right Coronary Aortic Cusp, Dilatation of the Sinus of Valsalva, and Ventricular Septal Defect." J thorac Cardiovasc Surg. Feb. 1997;113(2):253-60.

* cited by examiner

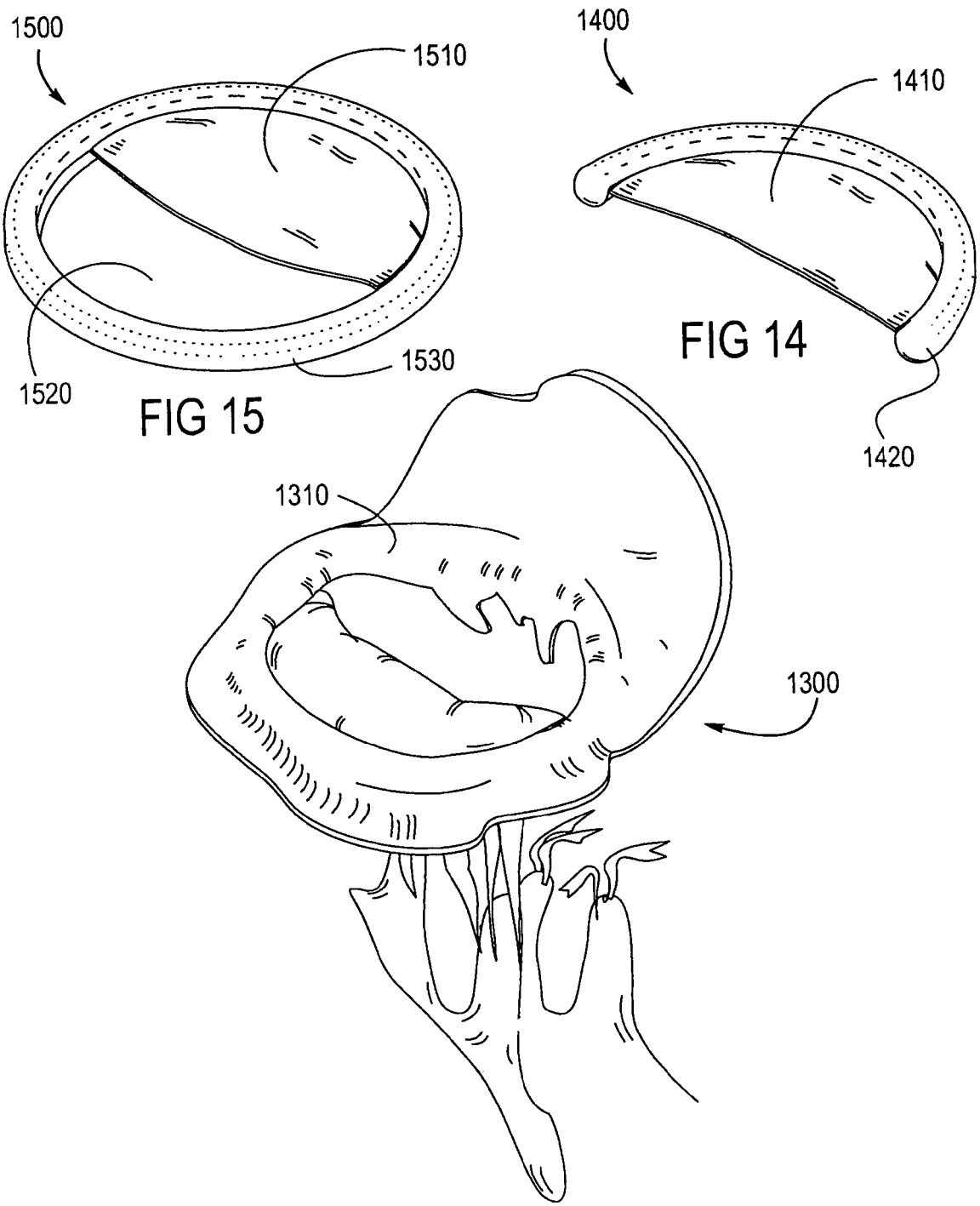

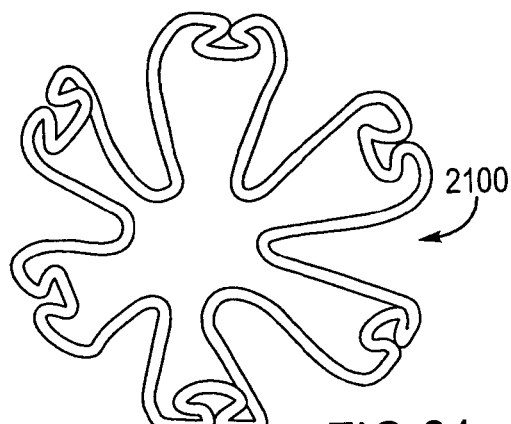
FIG 21
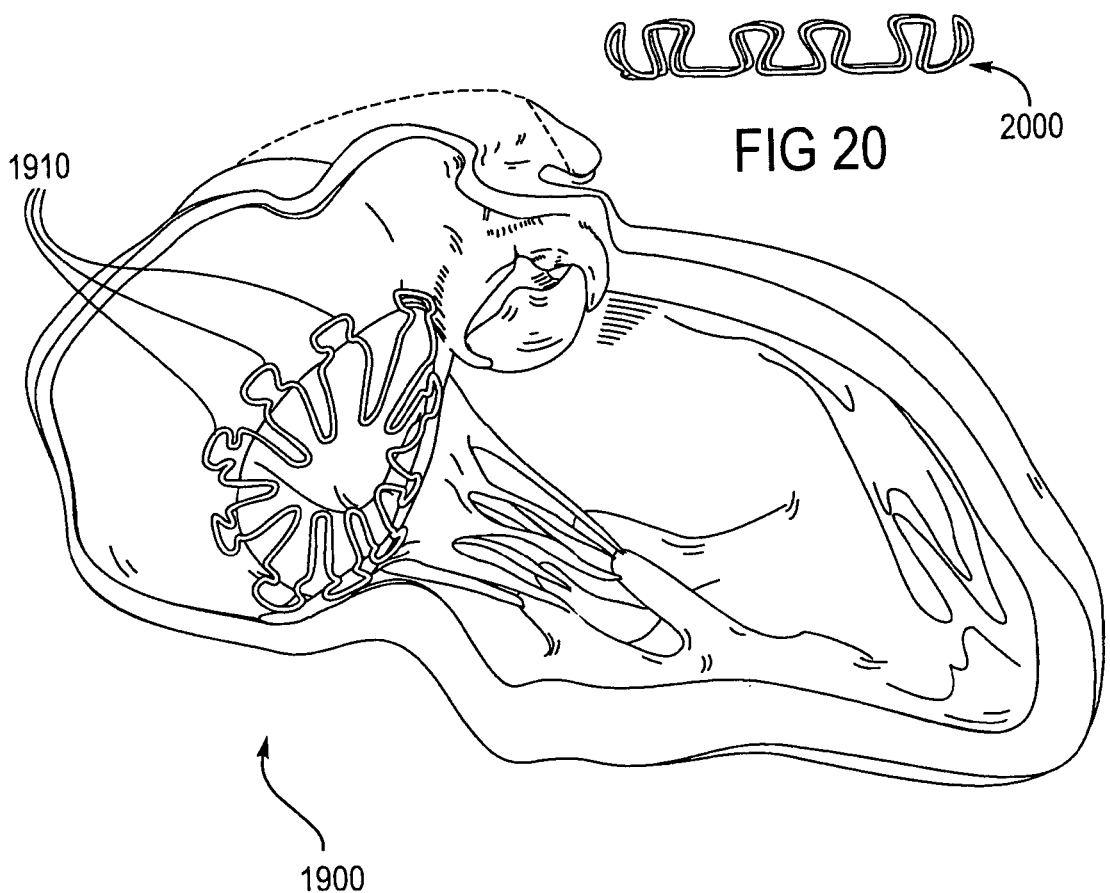
FIG 20
FIG 19

METHODS AND DEVICES FOR HEART VALVE TREATMENTS

RELATED APPLICATIONS

This application is a continuation of International Patent Application Ser. No. PCT/US02/31376, enticed "Methods and Devices for Heart Valve Treatment", having an international filing date of Oct. 1, 2002 and a priority date of Oct. 1, 2001, based upon the benefit of United States Provisional Patent Application Ser. No. 60/326,590, filed Oct. 1, 2001 and entitled "Methods and Systems for Heart Chamber Endocardial and Epicardial Scaffold Therapies."

FIELD OF THE INVENTION

This invention relates to methods and devices to improve the function of heart valves. More particularly, the invention relates to methods and devices to treat mitral valve regurgitation.

BACKGROUND OF THE INVENTION

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

The high pressure produced by contraction of the ventricle could push the valve leaflets too much and evert them. Prolapse is a term used to describe this condition. This is normally prevented by contraction of the papillary muscles within the ventricle, which are connected to the mitral valve leaflets by the chordae tendineae (chords). Contraction of the papillary muscles is simultaneous with the contraction of the ventricle and serves to keep healthy valve leaflets tightly shut at peak contraction pressures exerted by the ventricle.

Valve malfunction can result from the chords becoming stretched, and in some cases tearing. When a chord tears, the result is a flailed leaflet. Also, a normally structured valve may not function properly because of an enlargement of the valve annulus. This condition is referred to as a dilation of the annulus and generally results from heart muscle failure. In addition, the valve may be defective at birth or because of an acquired disease.

SUMMARY OF THE INVENTION

The present invention is a group of medical devices designed to improve heart valve function. The medical devices may be used individually, or in combination to supplement damaged valves, replace damaged valves, or improve damaged valves function. The medical devices include leaflet retainers, a neo-annulus, neo-leaflet, and a framework. In addition, the present invention includes novel methods for surgically treating heart valves.

BRIEF DESCRIPTION OF THE DRAWINGS

FIG. 13 shows a perspective view of a damaged native anterior leaflet 1310 that is not connected to the chordae tendineae.

FIG. 14 shows a perspective view of a device 1400 having a half sewing ring 1420 with a membrane 1410 that serves as a neo-annulus or a neo-leaflet.

FIG. 15 shows a perspective view of a device 1500 having a full sewing ring 1530 with a membrane 1510 that serves as a neo-annulus or a neo-leaflet.

FIG. 19 shows a perspective view of a leaflet retainer 1900 that is positioned on top of both native mitral valve leaflets.

FIG. 20 shows a side view of the embodiment shown in FIG. 19.

FIG. 21 shows a perspective view of the embodiment shown in FIG. 19.

DETAILED DESCRIPTION

Figure 1:
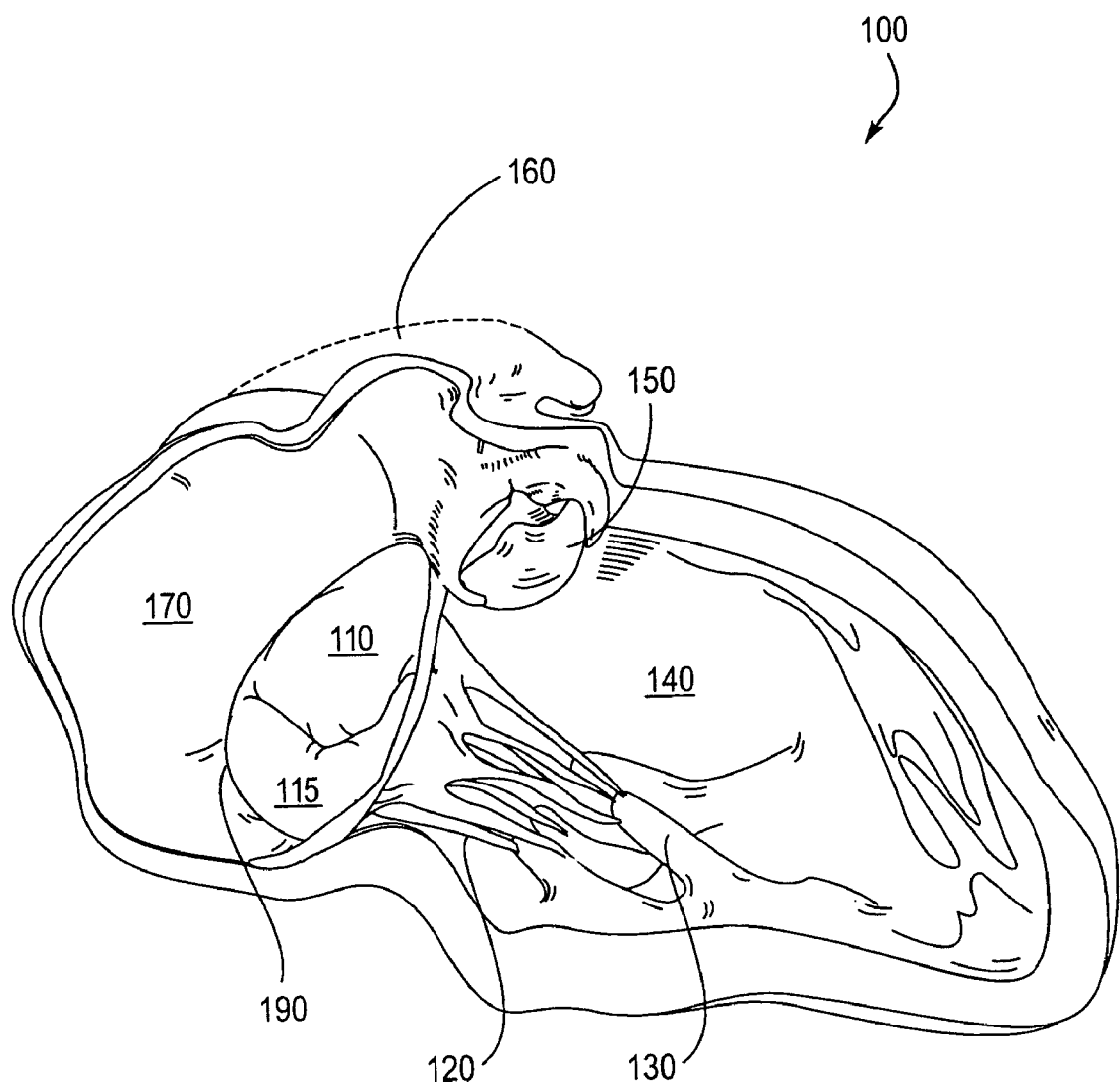
FIG. 1 shows a posterior oblique cutaway view of a patient's heart 100.

FIG. 1 shows a posterior oblique cutaway view of a patient's heart 100. Two of the four heart chambers are shown, the left atrium 170, and the left ventricle 140 (not shown are the right atrium and right ventricle). The left atrium 170 fills with blood from the pulmonary veins. The blood then passes through the mitral valve (also known as the bicuspid valve, and more generally known as an atrioventricular valve) during ventricular diastole and into the left ventricle 140. During ventricular systole, the blood is then ejected out of the left ventricle 140 through the aortic valve 150 and into the aorta 160. At this time, the mitral valve should be shut so that blood is not regurgitated back into the left atrium. The mitral valve consists of two leaflets, an anterior leaflet 110, and a posterior leaflet 115, attached to chordae tendineae 120 (hereafter, chords), which in turn are connected to papillary muscles 130 within the left ventricle 140. Typically, the mitral valve has a D-shaped anterior leaflet 110 oriented toward the aortic valve, with a crescent shaped posterior leaflet 115. The leaflets intersect with the atrium 170 at the mitral annulus 190.

Figure 2:
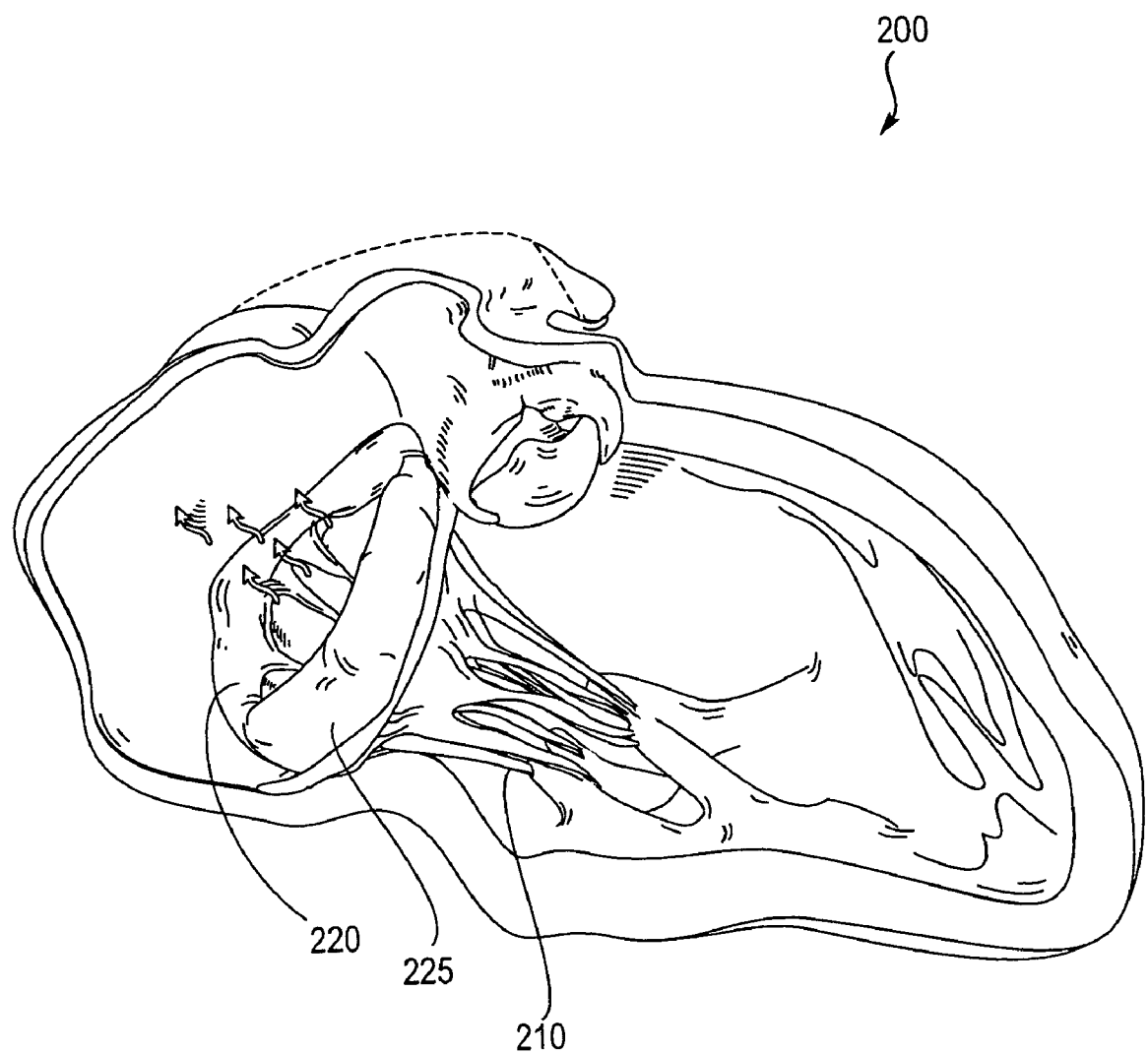
FIG. 2 shows a cutaway view of a patient's heart 200 with a prolapsed mitral valve that does not form a tight seal during ventricular systole, and thus allows blood to be regurgitated back into the left atrium during ventricular contraction.

FIG. 2 shows a cutaway view of a patient's heart 200 with a prolapsed mitral valve that does not form a tight seal during ventricular systole, and thus allows blood to be regurgitated back into the left atrium during ventricular contraction. The anterior 220 and posterior 225 leaflets are shown being blown into the left atrium with arrows indicating the direction of regurgitant flow. Among other causes, regurgitation can result from stretched chords 210 that are too long to prevent the leaflets from being blown into the atrium. As a result, the leaflets do not form a tight seal and blood is regurgitated into the atrium.

Figure 3:
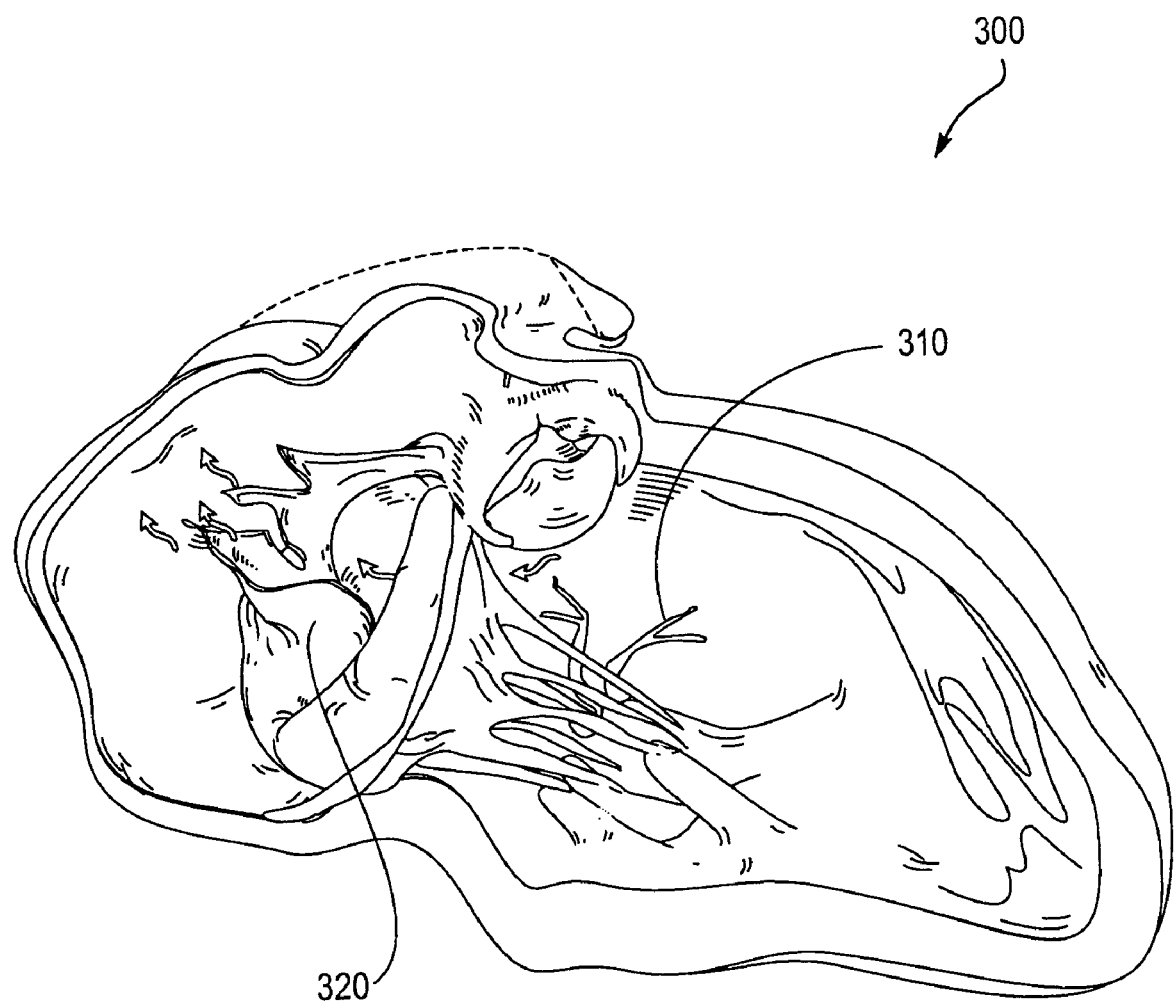
FIG. 3 shows a cutaway view of a patient's heart 300 with a flailing mitral valve 320 that does not form a tight seal during ventricular systole, and thus allows blood to be regurgitated back into the left atrium during ventricular contraction as indicated by arrows.

FIG. 3 shows a cutaway view of a patient's heart 300 with a flailing mitral valve 320 that does not form a tight seal during ventricular systole, and thus allows blood to be regurgitated back into the left atrium during ventricular contraction as indicated by arrows. Among other causes, regurgitation can result from torn chords 310.

Figure 4:
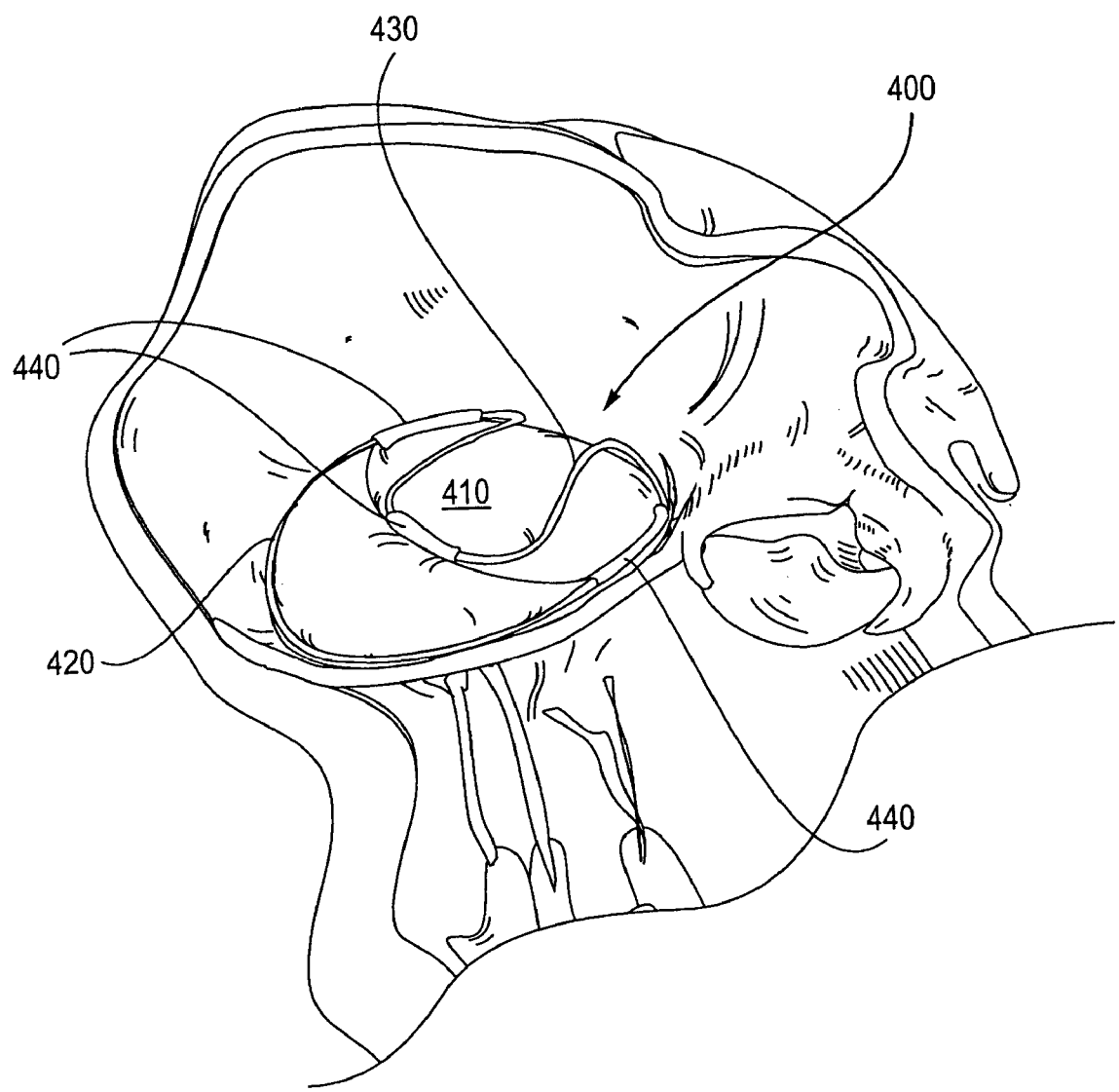
FIG. 4 shows a perspective view of a spring bridge neo-leaflet used to supplement or replace a native leaflet.

FIG. 4 shows a perspective view of a spring bridge neo-leaflet used to supplement or replace a native leaflet. The device 400 is shown to be formed of a base 420 that is positioned around the mitral annulus, and then closes in over the anterior leaflet to form a bridge 430 over the anterior leaflet. The bridge 430 may be a rigid, semi-rigid, or flexible. The bridge may act like a spring, and thus respond dynamically to pressure differentials within the heart. The bridge 430 may have a spanning material 410 that spans the bridge 430. The spanning material 410 may be attached to the device 400 with one or more attachment means 440 (for example, it may be sewn, glued, or welded to the device 400, or it may be attached to itself when wrapped around the device 400). The spanning material 410 maybe made from a synthetic material (for example, thin Nitinol, Dacron fabric, Polytetrafluoroethylene or PTFE, Silicone, or Polyurethane) or a biological material (for example, human or animal pericardium). The device 400 may be delivered percutaneously, through the chest (thoracoscopy), or using open heart surgical techniques. If delivered percutaneously, the device may be made from a super-elastic material (for example, Nitinol) enabling it to be folded and collapsed such that it can be delivered in a catheter, and will subsequently self-expand when released from the catheter. The device may be secured to the mitral annulus with sutures or other attachment means (i.e. barbs, hooks, staples, etc).

Figure 5:
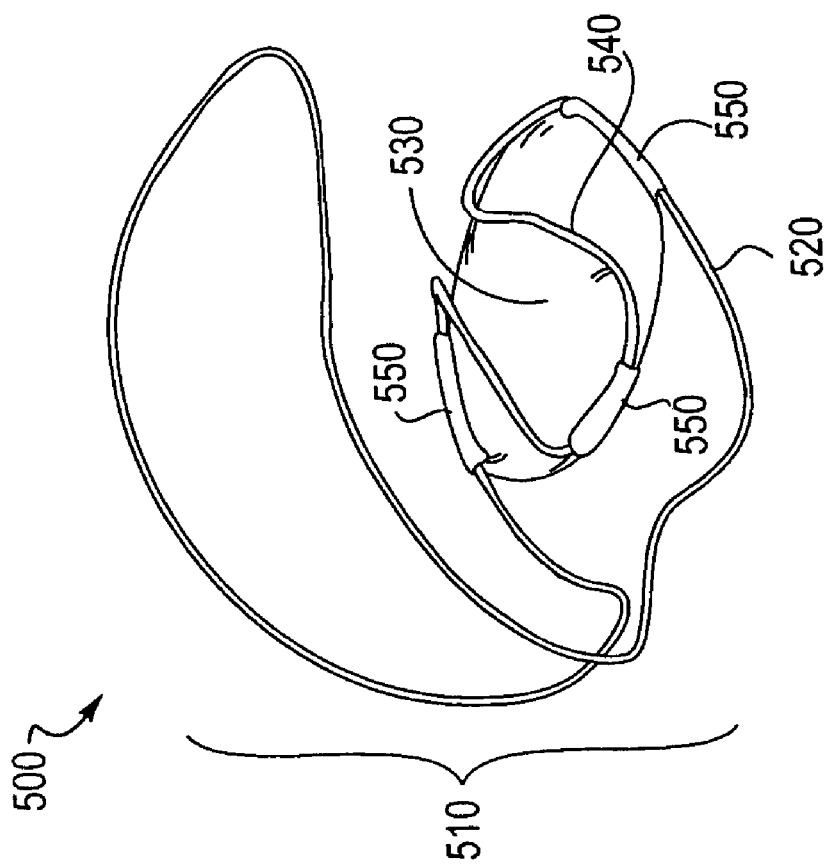
FIG. 5 shows a perspective view of an embodiment of the invention comprised of a bridge 540, spanning material 530, attachment means 550, and a base 520. In addition, the device is shown to have a framework 510.

FIG. 5 shows a perspective view of an embodiment of the invention comprised of a bridge 540, spanning material 530, attachment means 550, and a base 520. In addition, the device is shown to have a framework 510. Preferably the framework 510 does not interfere with atrial contractions, instead contracting with the atrium. As such, the device 500 may have non-uniform flexibility to improve its function within the heart. The framework is shown here rising from the base 520 with two substantially parallel arched wires that connect to form a semicircular hoop above the base 520. The framework 510 helps to accurately position the device within the atrium, and also helps to secure the device within the atrium. The neo-leaflet comprised of the bridge 540 and spanning material 530 is shown in the closed valve position.

Figure 6:
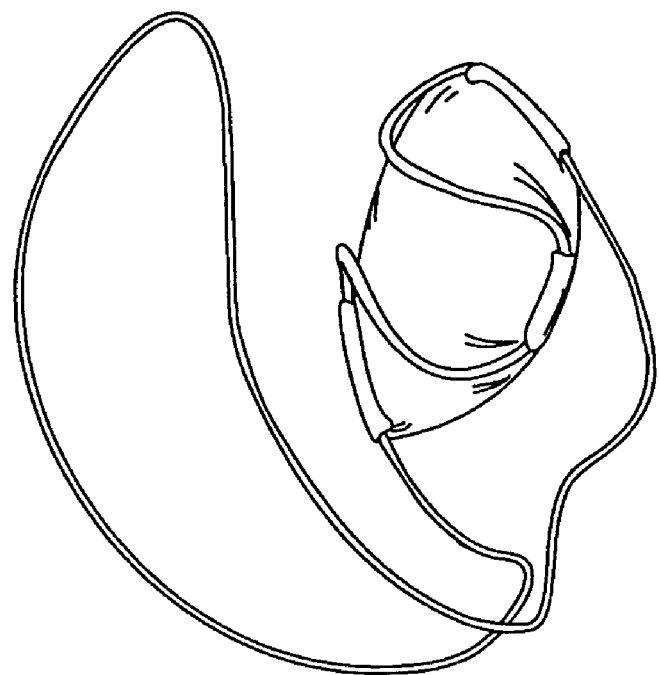
FIG. 6 shows a perspective view of the embodiment of FIG. 5 in the open valve position.

FIG. 6 shows a perspective view of the embodiment of FIG. 5 in the open valve position.

Figure 7:
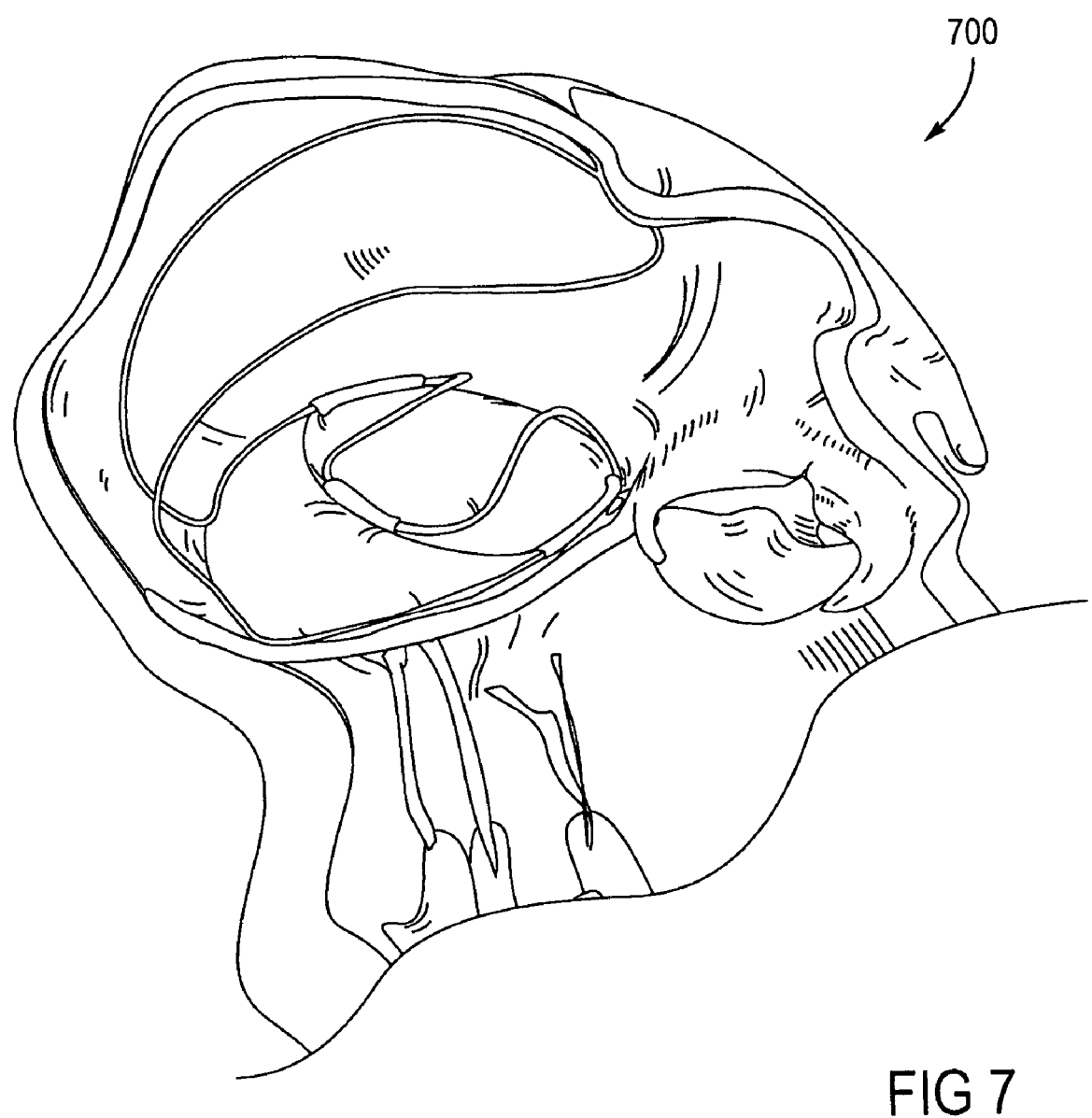
FIG. 7 shows a perspective view of the embodiments shown in FIGS. 5 and 6 positioned within the left atrium of the heart.

FIG. 7 shows a perspective view of the embodiments shown in FIGS. 5 and 6 positioned within the left atrium of the heart.

Figure 8:
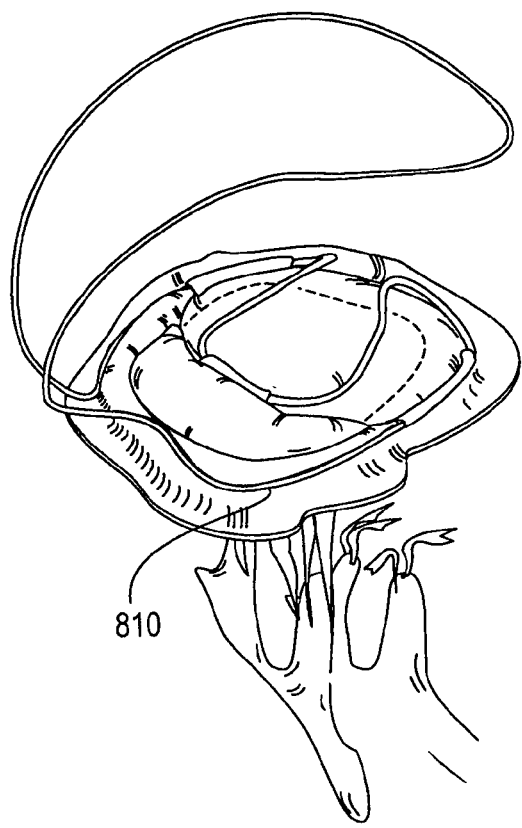
FIGS. 8 and 9 show a perspective view of the embodiments of FIGS. 5 and 6 positioned within the left atrium of the heart.
Figure 9:
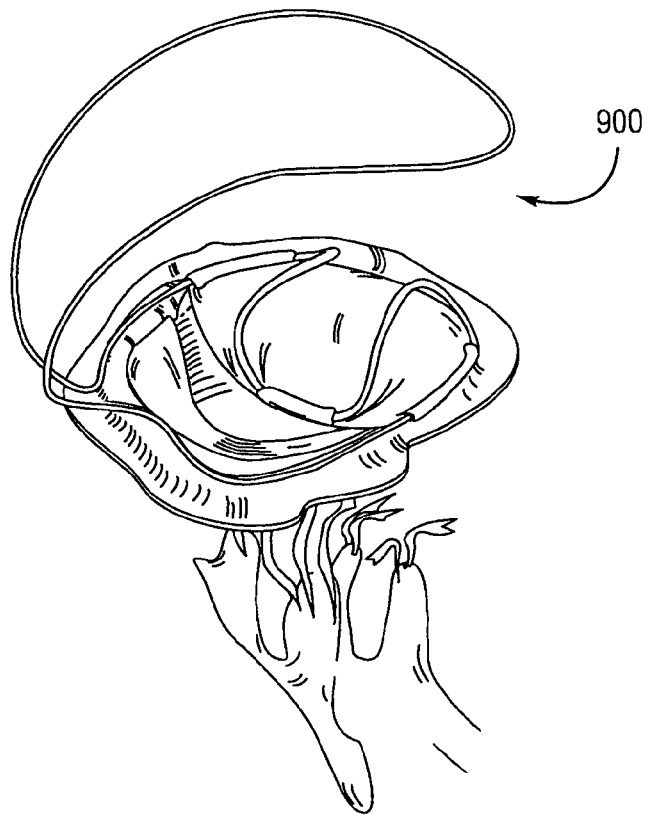

FIGS. 8 and 9 show a perspective view of the embodiments of FIGS. 5 and 6 positioned within the left atrium of the heart. FIG. 8 shows the embodiment in a closed valve position, and FIG. 9 shows the embodiment in an open valve position. The sizing of the base 810 can vary depending upon the patient's needs.

Figure 10:
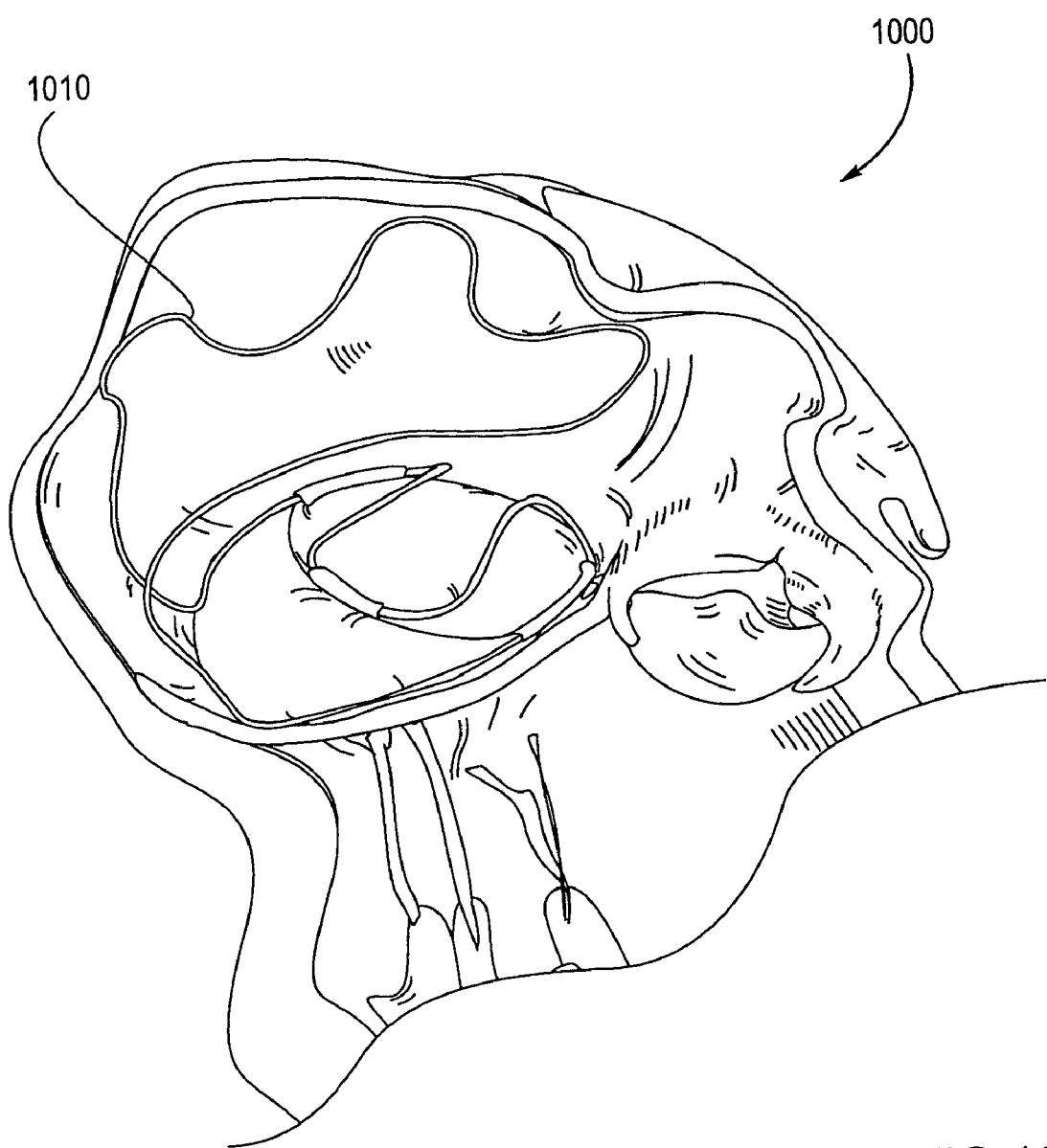
FIG. 10 shows a perspective view of an embodiment of the invention having a framework 1010 that avoids the pulmonary veins (not shown).

FIG. 10 shows a perspective view of an embodiment of the invention having a framework 1010 that avoids the pulmonary veins (not shown).

Figure 11:
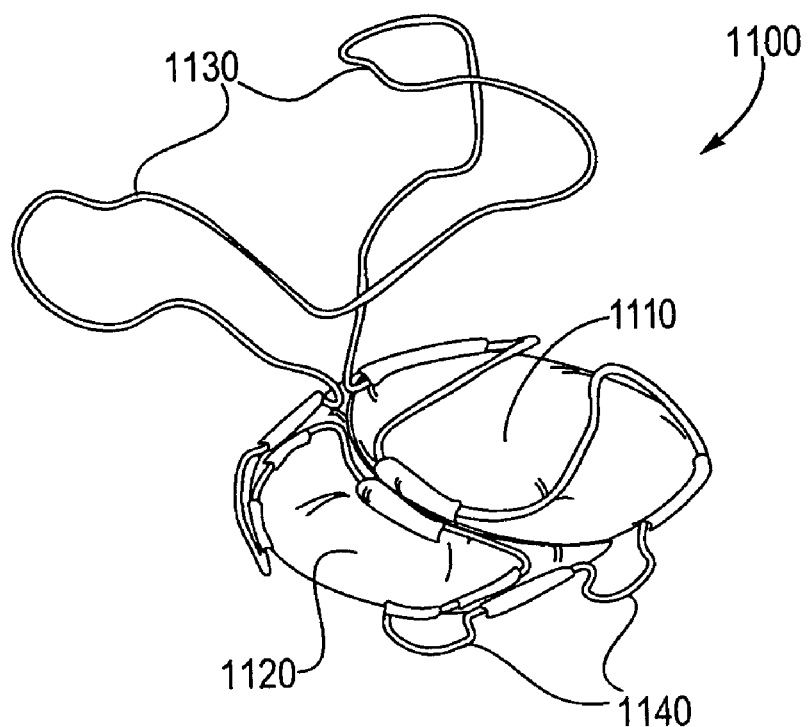
FIGS. 11 and 12 show a perspective view of a dual spring bridge neo-leaflet having an anterior bridge spanned by an anterior material 1110, and a posterior bridge spanned by a posterior material 1120.
Figure 12:
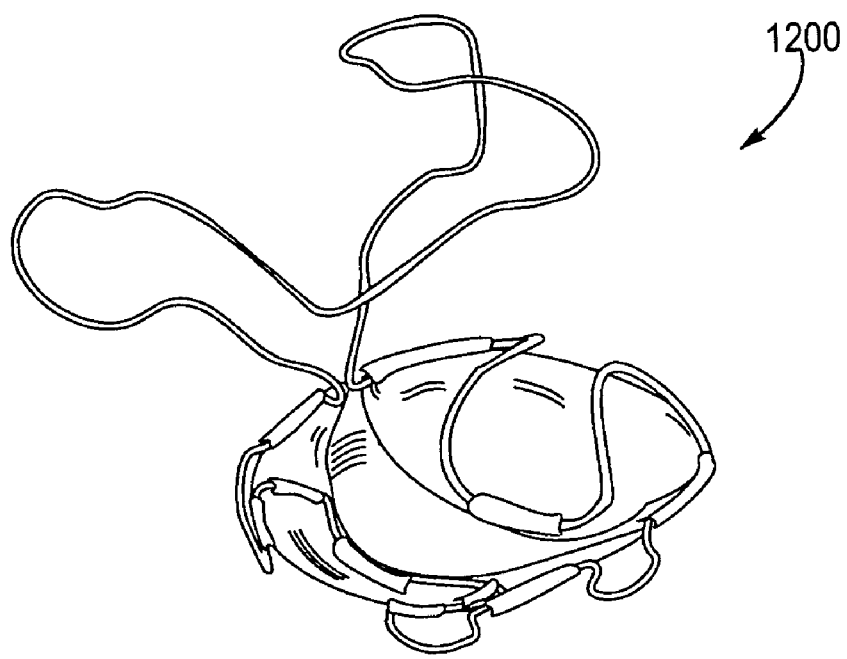

FIGS. 11 and 12 show a perspective view of a dual spring bridge neo-leaflet have an anterior bridge spanned by an anterior material 1110, and a posterior bridge spanned by a posterior material 1120. The framework 1130 shown here illustrates an alternative design. This embodiment also illustrates a base having clips 1140 that protrude below an imaginary plane formed by the annulus of the valve. FIG. 11 shows the dual neo-leaflets in a closed valve position, and FIG. 12 shows the dual neo-leaflets in an open valve position.

FIG. 13 shows a perspective view of a damaged native anterior leaflet 1310 that is not connected to the chordae tendineae.

FIG. 14 shows a perspective view of a device 1400 having a half sewing ring 1420 with a membrane 1410 that serves as a neo-annulus or a neo-leaflet. When serving as a neo-annulus, the membrane 1410 is a relatively immobile structure covering one of the native valve leaflets, particularly a damaged, missing or nonfunctional leaflet. The neo-annulus serves to extend the native annulus and coapts with the remaining functional native leaflet to create a functioning mitral valve. When serving as a neo-leaflet, the membrane 1410 is a mobile structure that moves in response to blood flow, coapting with one of the native leaflets to create a functioning mitral valve. The neo-leaflet replaces the function of a damaged, missing or nonfunctional native leaflet. The device 1400 is attached to the mitral valve annulus via the half sewing ring 1420. This embodiment could be surgically attached to the valve annulus and/or combined with a framework for anchoring the device within the patient's atrium using catheter based intraluminal techniques.

FIG. 15 shows a perspective view of a device 1500 having a full sewing ring 1530 with a membrane 1510 that serves as a neo-annulus or a neo-leaflet. The device 1500 has an opening 1520 though the sewing ring 1530 opposite the membrane 1510 for blood flow. Alternatively, this embodiment could have two neo-leaflets. This embodiment could be surgically attached to the valve annulus and/or combined with a framework for anchoring the device within the patient's atrium using catheter based intraluminal techniques.

Figure 16:
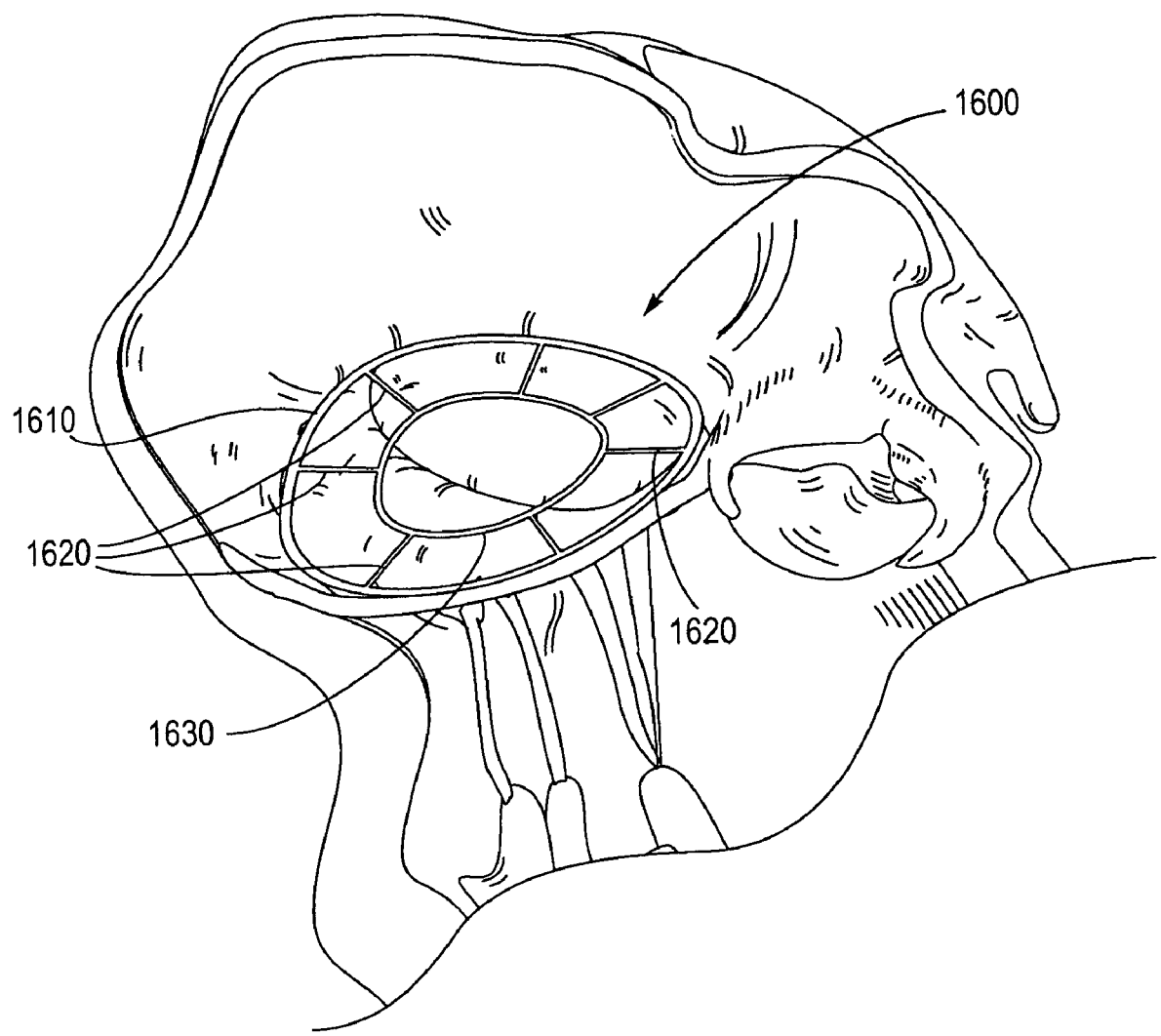
FIG. 16 shows a perspective view of a leaflet retainer 1600 that is positioned within the atrium on top of both native mitral valve leaflets.

FIG. 16 shows a perspective view of a leaflet retainer 1600 that is positioned within the atrium on top of both native mitral valve leaflets. This embodiment is comprised of an outer ring 1610 and an inner ring 1630 connected by radial struts 1620. The interior region of the valve orifice remains unobstructed to blood flow with this embodiment. This embodiment could be surgically attached to the valve annulus and/or combined with a framework for anchoring the device within the patient's atrium using catheter based intraluminal techniques.

Figure 17:
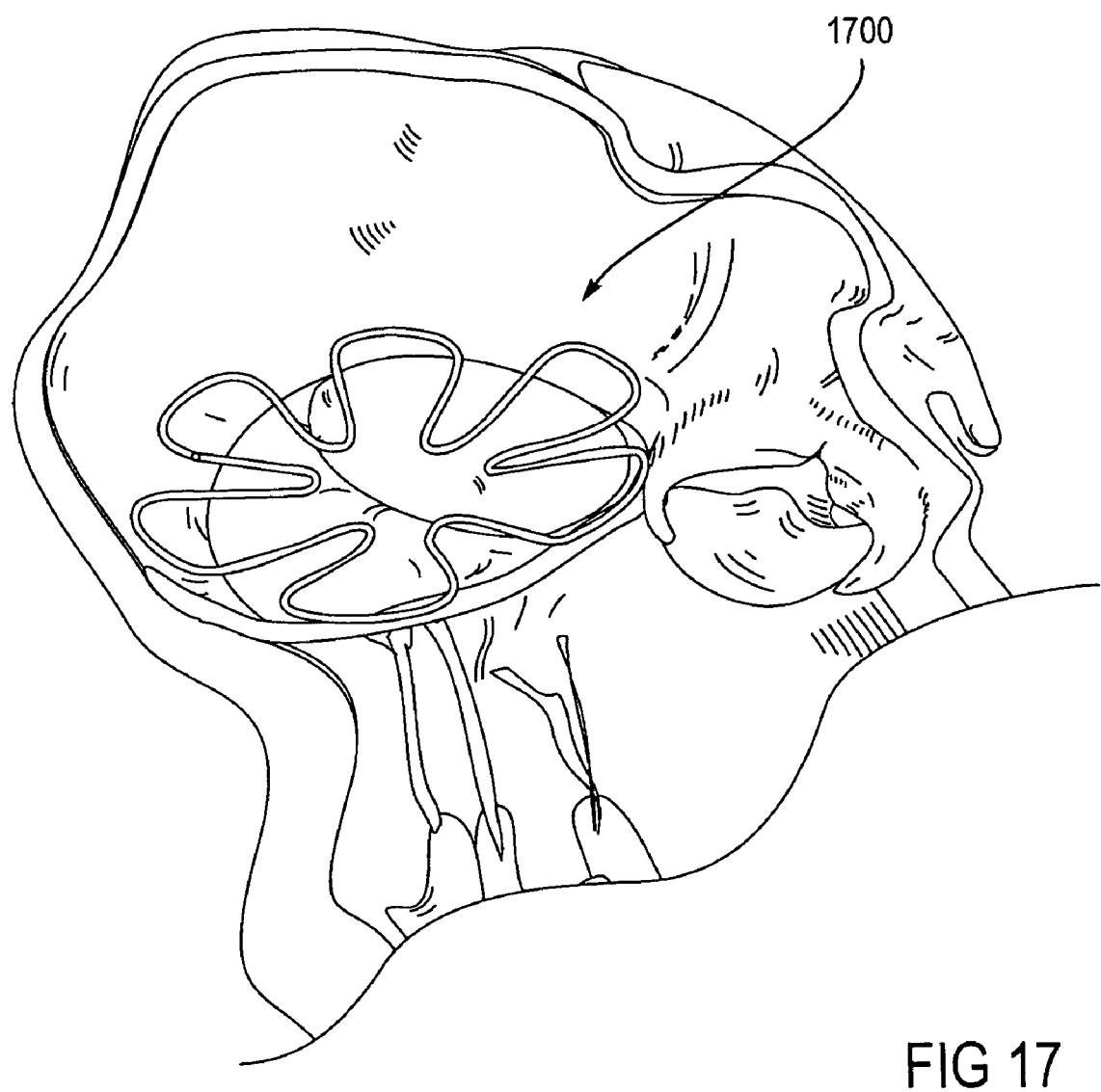
FIG. 17 shows a perspective view of a leaflet retainer 1700 that is positioned within the atrium on top of both native mitral valve leaflets.

FIG. 17 shows a perspective view of a leaflet retainer 1700 that is positioned within the atrium on top of both native mitral valve leaflets. This embodiment could be surgically attached to the valve annulus and/or combined with a framework for anchoring the device within the patient's atrium using catheter based intraluminal techniques.

Figure 18:
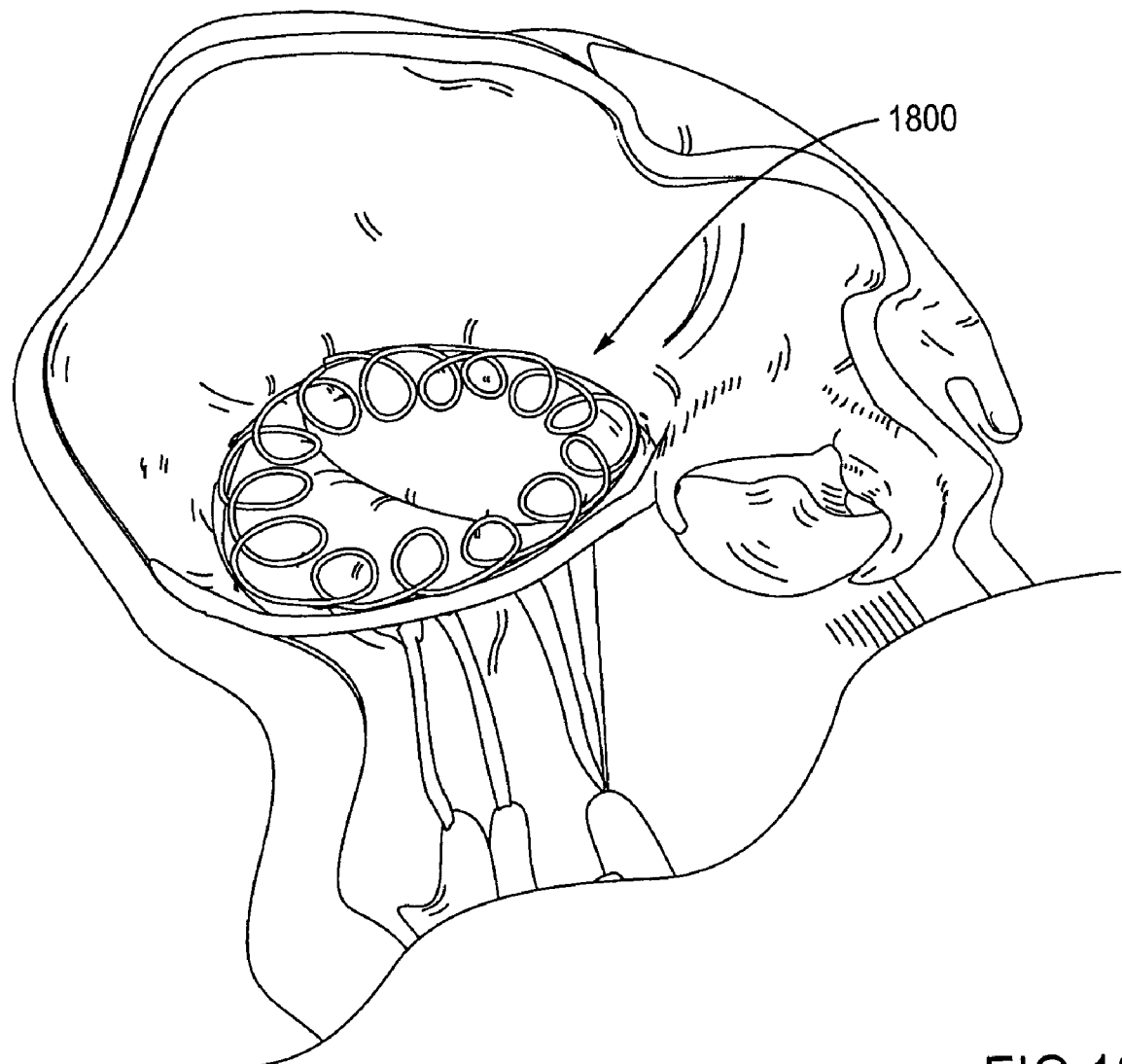
FIG. 18 shows a perspective view of a leaflet retainer 1800 that is positioned within the atrium on top of both native mitral valve leaflets.

FIG. 18 shows a perspective view of a leaflet retainer 1800 that is positioned within the atrium on top of both native mitral valve leaflets. This embodiment could be surgically attached to the valve annulus and/or combined with a framework for anchoring the device within the patient's atrium using catheter based intraluminal techniques.

FIG. 19 shows a perspective view of a leaflet retainer 1900 that is positioned on top of both native mitral valve leaflets. Alternatively, the leaflet retainers may be designed to retain only one leaflet, or a portion of a leaflet, depending on patient needs. The outer sections of this embodiment have anchors 1910 that distribute stresses along the atrial wall, helping to prevent erosion of the atrial walls. This embodiment could be surgically attached to the valve annulus and/or combined with a framework for anchoring the device within the patient's atrium using catheter based intraluminal techniques.

FIG. 20 shows a side view of the embodiment shown in FIG. 19.

FIG. 21 shows a perspective view of the embodiment shown in FIG. 19.

Figure 22:
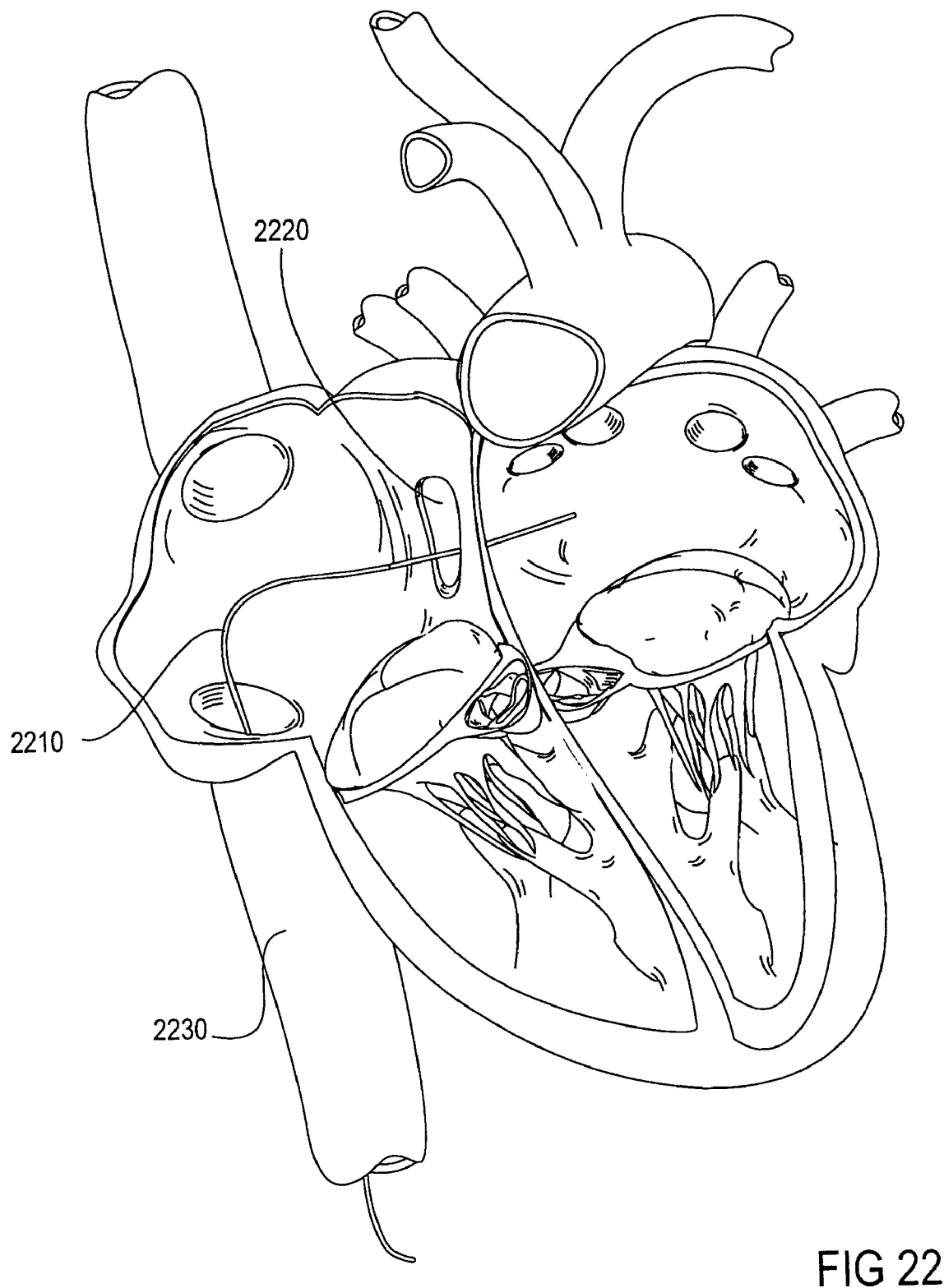
FIGS. 22 through 26 show the sequence of steps for a catheter-based percutaneous deployment of an embodiment of the invention.
Figure 23:
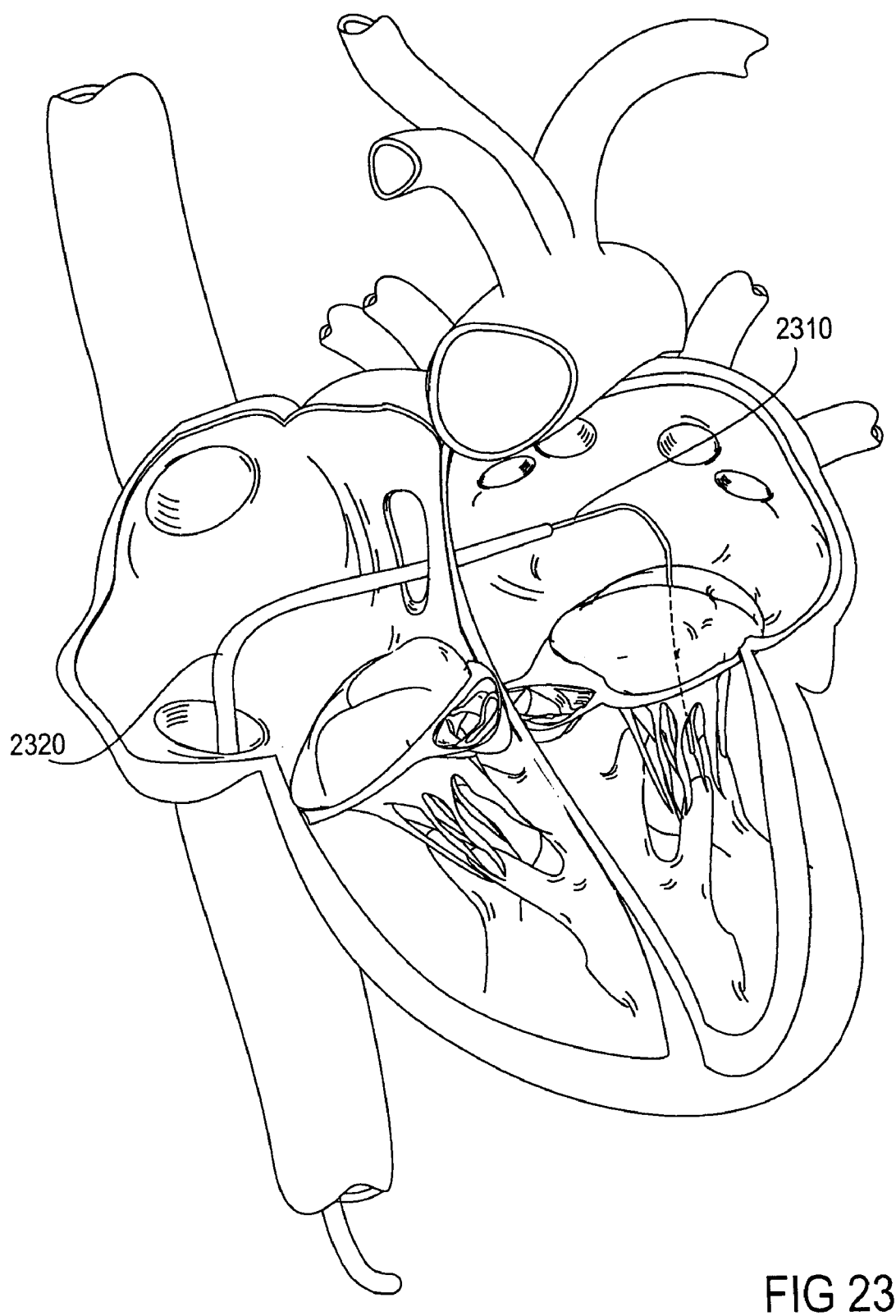
Figure 24:
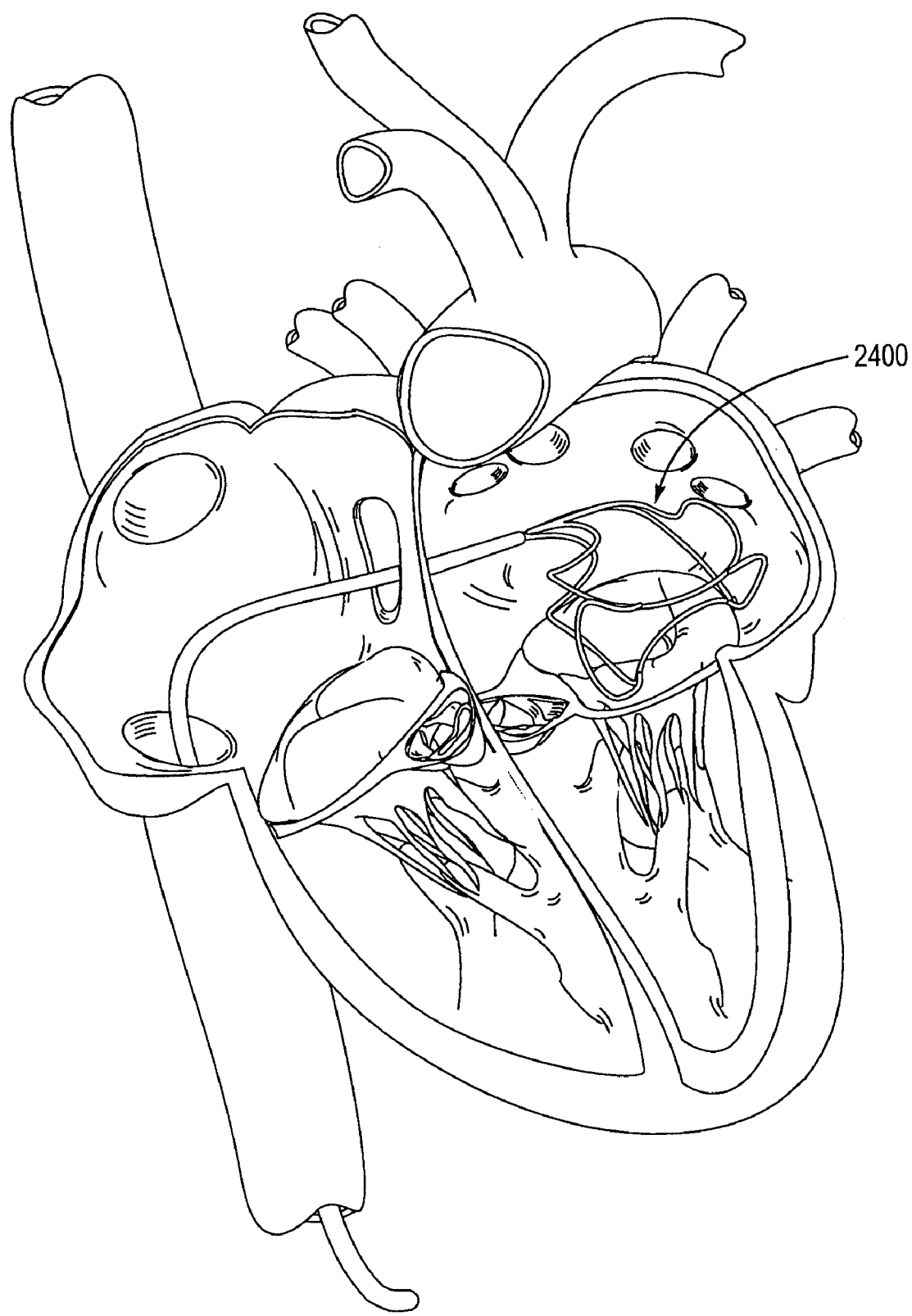
Figure 25:
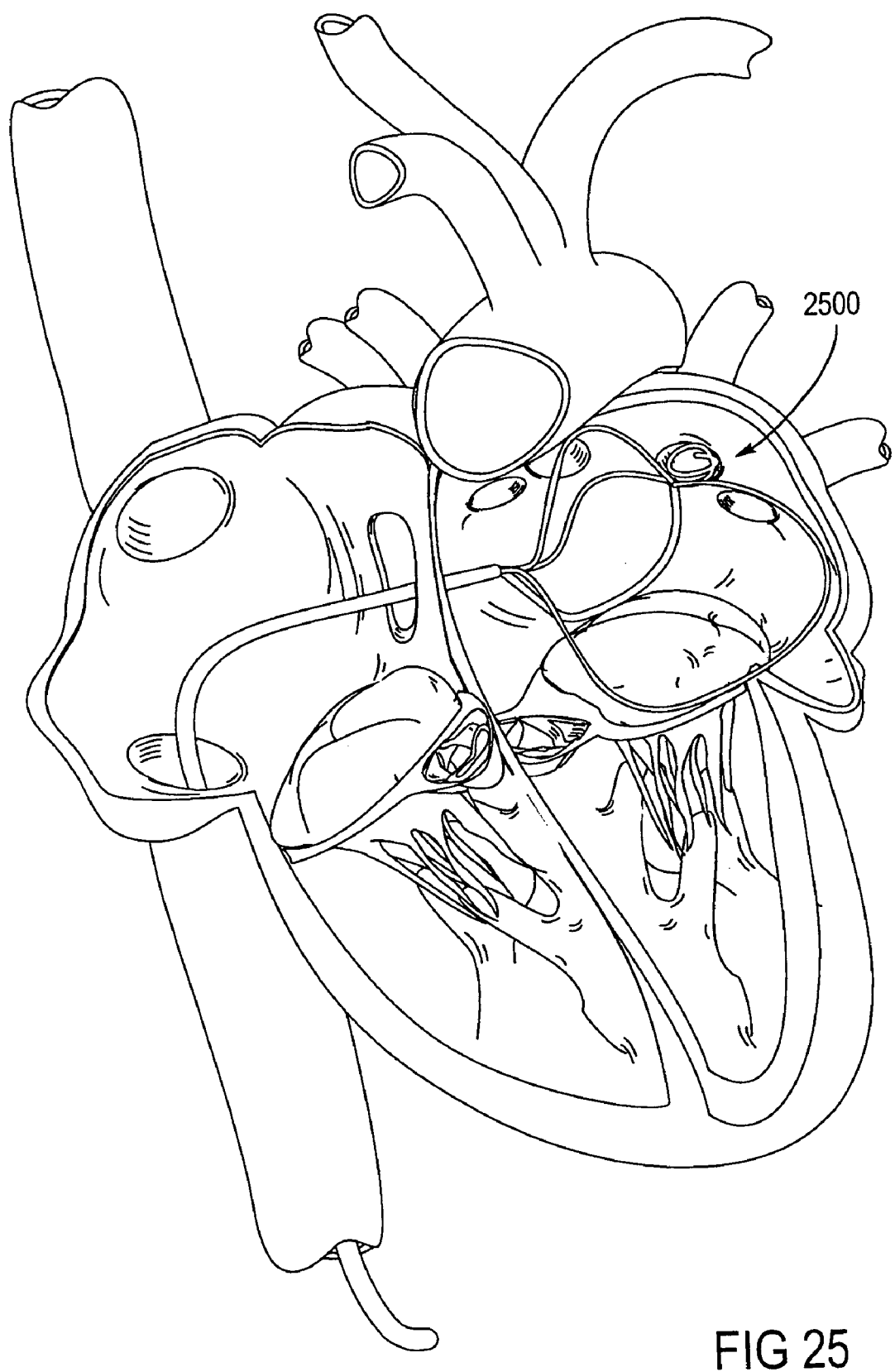
Figure 26:
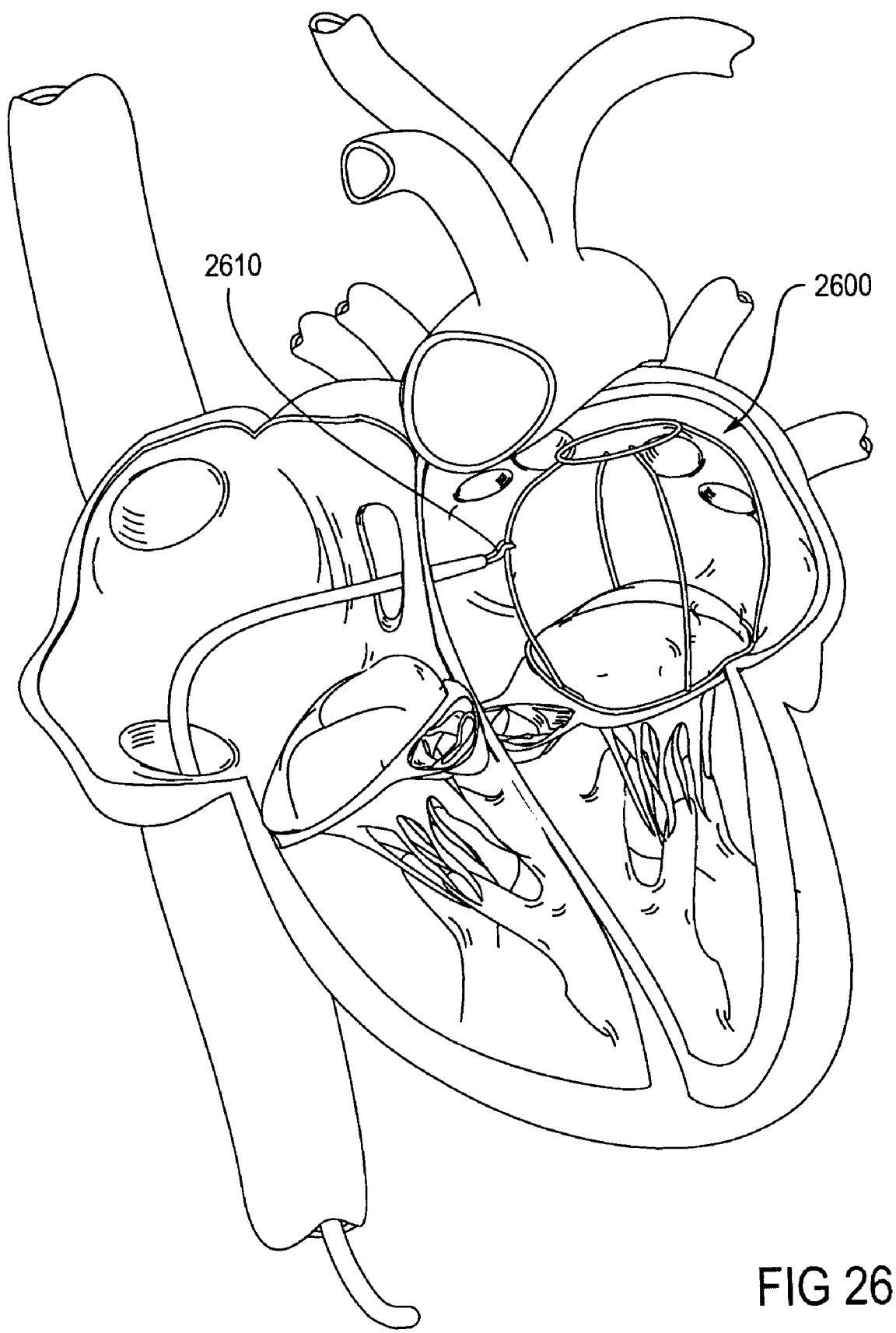

FIGS. 22 through 26 show the sequence of steps for a catheter-based percutaneous deployment of an embodiment of the invention. This deployment technique applies to other embodiments as well. Initially, a guidewire is introduced into the vasculature via a peripheral venous access site, such as the femoral or jugular vein, or alternatively by means of surgical access through the right atrium. FIG. 22 shows the introduction of a guidewire 2210 through the septum 2220 between the right and left atria. The guidewire is shown being introduced into the right atrium via the inferior vena cava 2230. FIG. 23 shows a catheter 2320 being advanced over the guidewire 2310. FIG. 24 shows an embodiment of the invention 2400 being released from the catheter after the guidewire has been removed. Alternatively, a guidewire could be used to place the device. FIG. 25 shows an embodiment of the invention having an additional feature, a looped eyelet 2500 that is being placed within a pulmonary vein to help position the device within the atrial chamber. The looped eyelet 2500 could be advanced over a guidewire. FIG. 26 shows an embodiment of the invention 2600 being positioned within the left atrium. The device 2600 can be positioned or repositioned within the atrium using a catheter deployed grasping instrument 2610.

Figure 27:
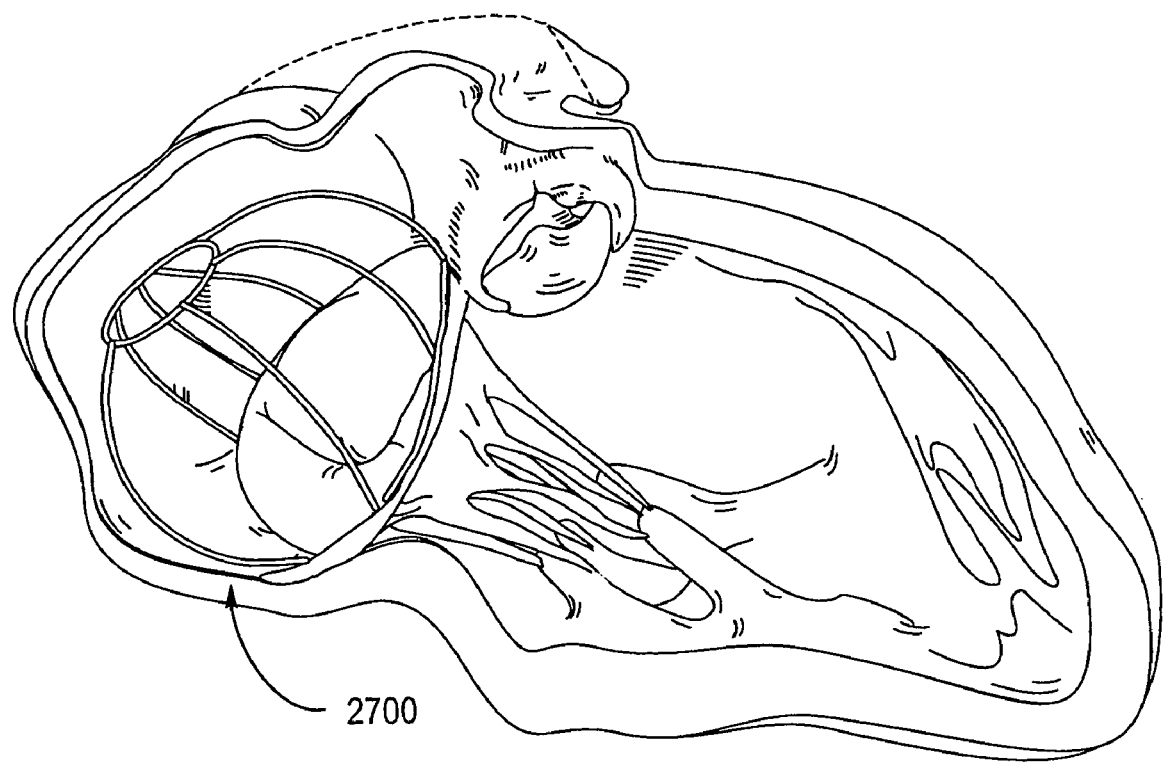
FIG. 27 shows a perspective view of an embodiment of the invention 2700 having a framework that partially fills the atrium.

FIG. 27 shows a perspective view of an embodiment of the invention 2700 having a framework that partially fills the atrium.

Figure 28:
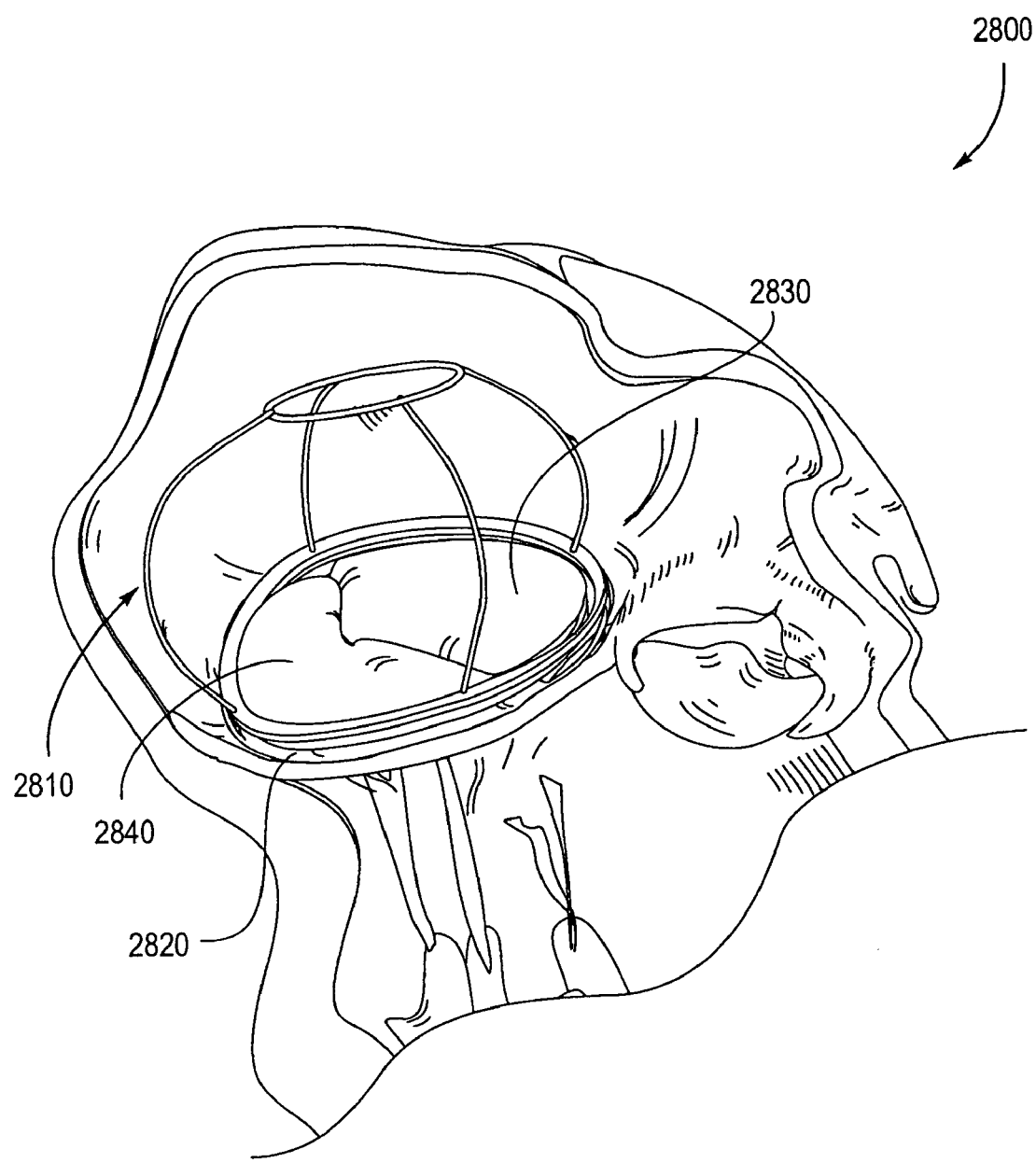
FIG. 28 shows a perspective view of an embodiment of the invention 2800 having dual neo-leaflets, 2830 and 2840.

FIG. 28 shows a perspective view of an embodiment of the invention 2800 having dual neo-leaflets, 2830 and 2840. The device is comprised of a framework 2810 an annular base 2820, and the neo-leaflets, 2830 and 2840. The neo-leaflets supplement or replace native leaflets, and thus function as a one-way valve to allow blood to flow from the atrium to the ventricle, and to prevent blood from flowing from the ventricle to the atrium. This is accomplished because the neo-leaflets structure is similar to native leaflet structure.

Figure 29:
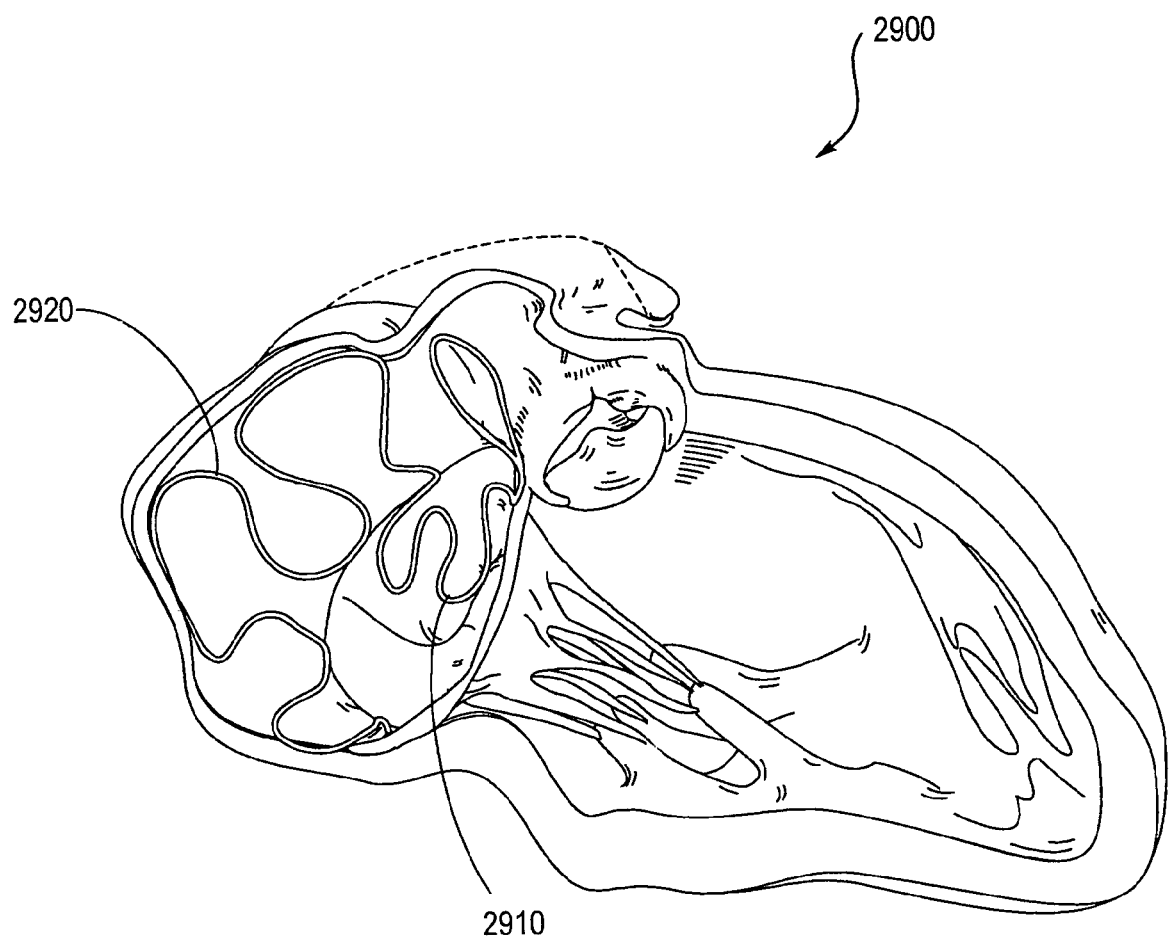
FIG. 29 shows a perspective view of an embodiment of the invention 2900 having a leaflet retainer 2910 positioned against a native leaflet as well as a framework structure 2920 that meanders about the atrium without interfering with the pulmonary veins.

FIG. 29 shows a perspective view of an embodiment of the invention 2900 having a leaflet retainer 2910 positioned against a native leaflet as well as a framework structure 2920 that meanders about the atrium without interfering with the pulmonary veins. The leaflet retainer 2910 prevents the leaflet from prolapsing into the atrium due to the pressure differential during ventricular contractions, thus improving closure of the mitral valve and reducing regurgitation.

Figure 30:
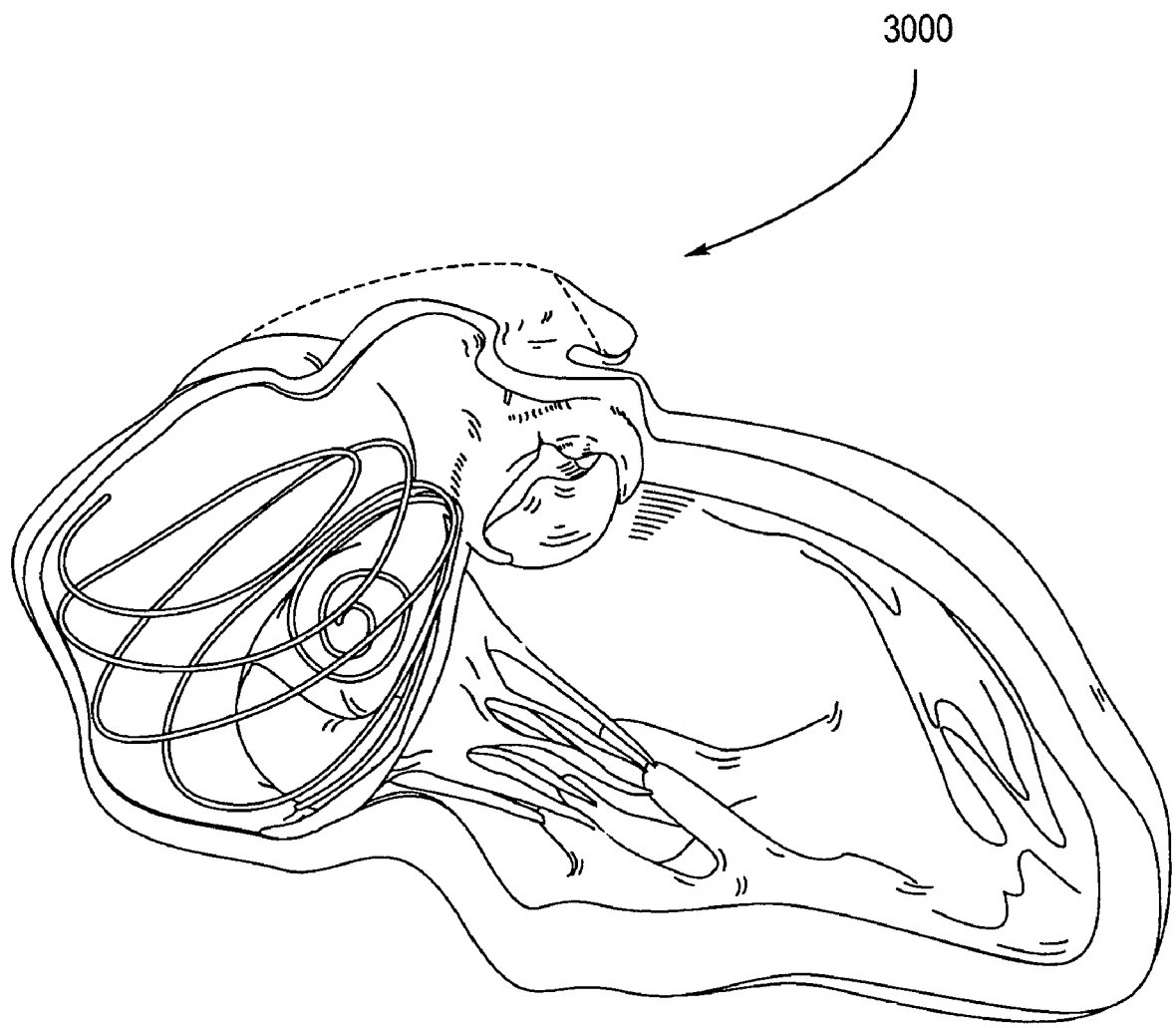
FIG. 30 shows a perspective view of another embodiment of the invention 3000 consisting of a continuous wire or tube that forms a leaflet retainer and framework.

FIG. 30 shows a perspective view of another embodiment of the invention 3000 consisting of a continuous wire or tube that forms a leaflet retainer and framework. The geometry of the framework is such that it spirals upward within the atrium. The device 3000 is secured in place because the framework expands within the atrium, and experiences mural pressures. The leaflet retainer is secured in place over a native leaflet by its coupling to the framework, and the leaflet retainer functions to prevent the native leaflet from experiencing prolapse. In addition, a coating that promotes tissue growth may aid in the fixation process of the framework within the atrium. However, the leaflet retainer section of the device 3000 may benefit from a coating that inhibits tissue growth, thus allowing the native leaflet to allow blood to flow into the ventricle.

Figure 31:
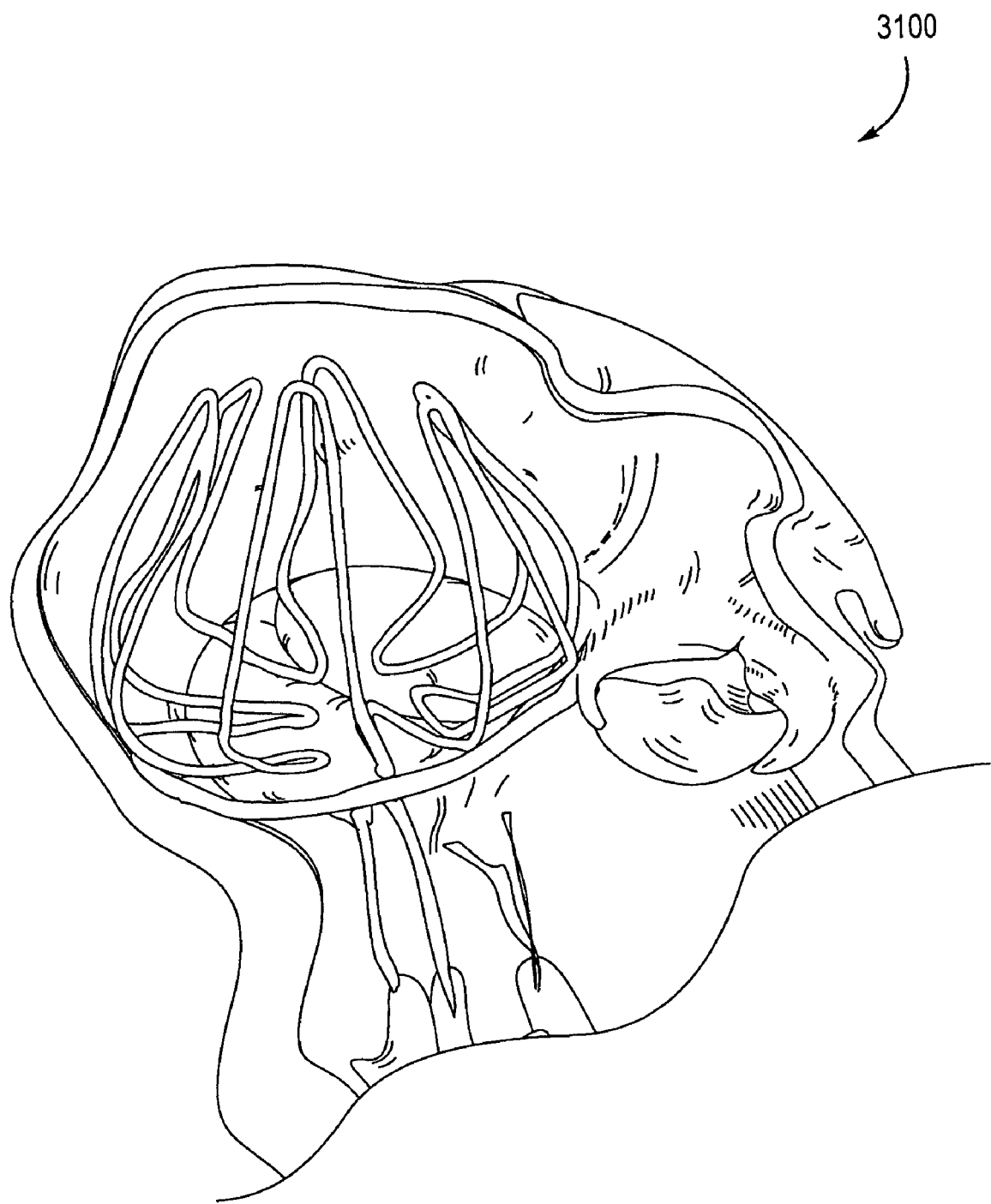
FIG. 31 shows a perspective view of a tulip shaped wire form configuration 3100 of the invention.

FIG. 31 shows a perspective view of a tulip shaped wire form configuration 3100 of the invention.

Figure 32:
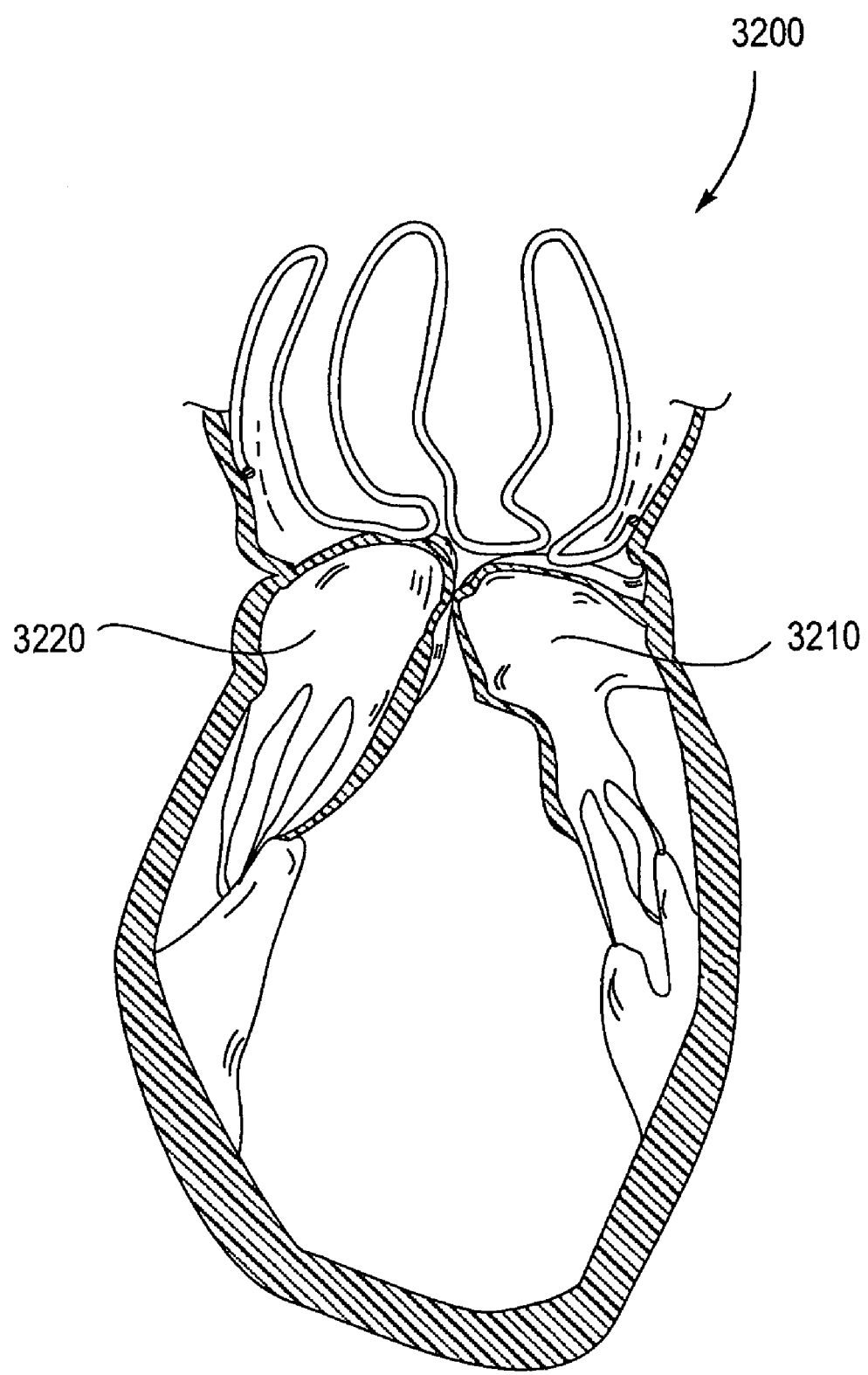
FIG. 32 shows cutaway view of a tulip shaped wire form configuration 3200 of the invention.

FIG. 32 shows cutaway view of a tulip shaped wire form configuration 3200 of the invention. The illustration shows the device 3200 making contact with native leaflets, 3220 and 3210, to prevent prolapse. The device 3200 is comprised of a leaflet retainer section that functions to prevent the native leaflets, 3210 and 3220, from being blown into the atrium when the ventricle contracts. The leaflet retaining section is positioned directly over the native leaflets. In this embodiment, the leaflet retaining aspect of the device 3200 is shown to be integrally formed with the framework section of the device. However, in other embodiments, the leaflet retainer and framework may be separate structures which can be deployed separately for individual use or in combination.

Figure 33:
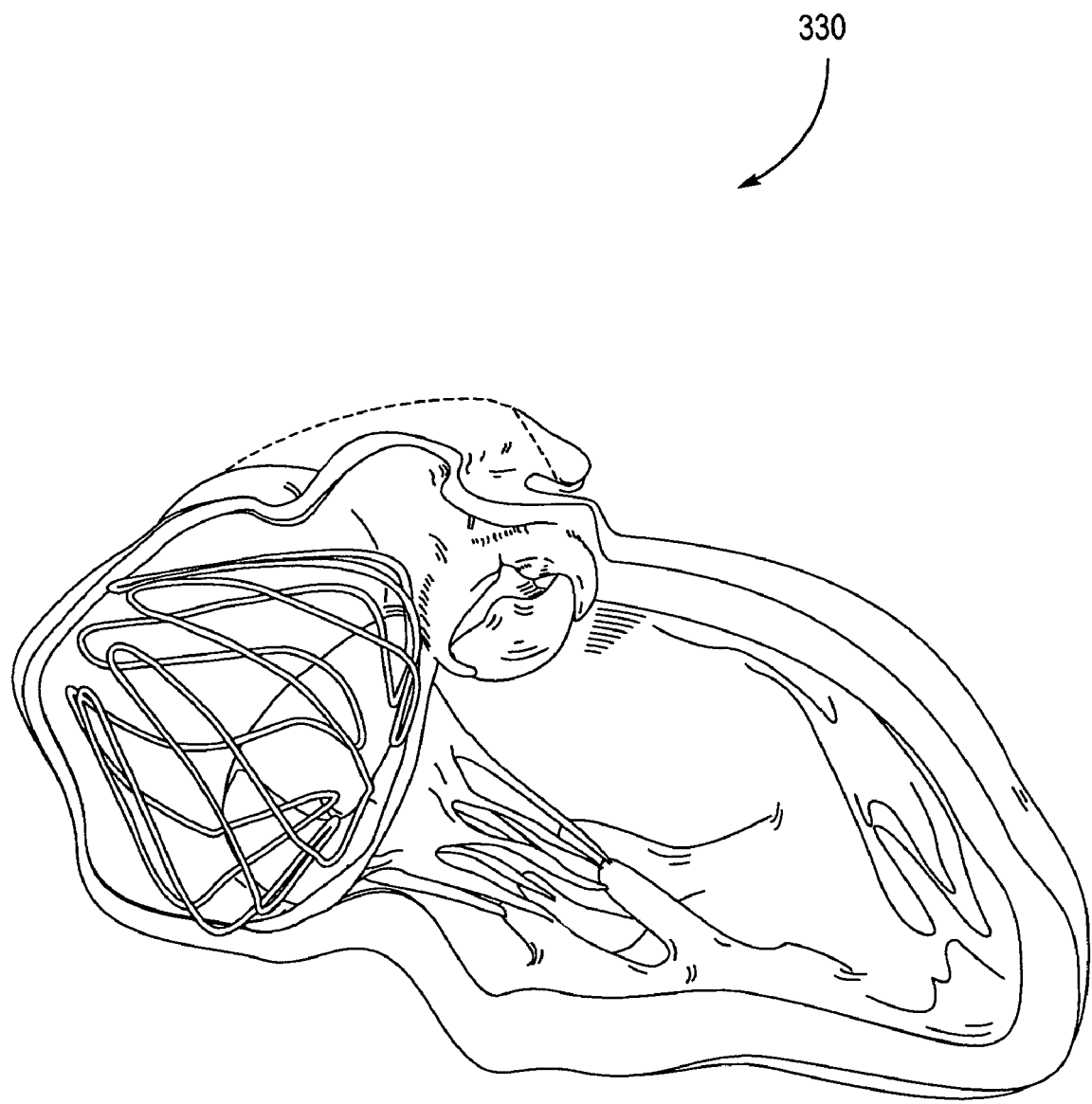
FIG. 33 shows a cutaway view of a tulip with a twist wire form configuration 3300 of the invention.

FIG. 33 shows a cutaway view of a tulip with a twist wire form configuration 3300 of the invention. The twist aspect enables the device to be shortened through twisting to decrease the longitudinal spring constant. The device 3300 is comprised of a leaflet retainer section that functions to prevent the native leaflets from being blown into the atrium when the ventricle contracts. The leaflet retaining section is positioned directly over the native leaflets. In this embodiment, the leaflet retaining aspect of the device 3300 is shown to be integrally formed with the framework section of the device. However, in other embodiments, the leaflet retainer and framework may be separate structures which can be deployed separately for individual use or in combination.

Figure 34:
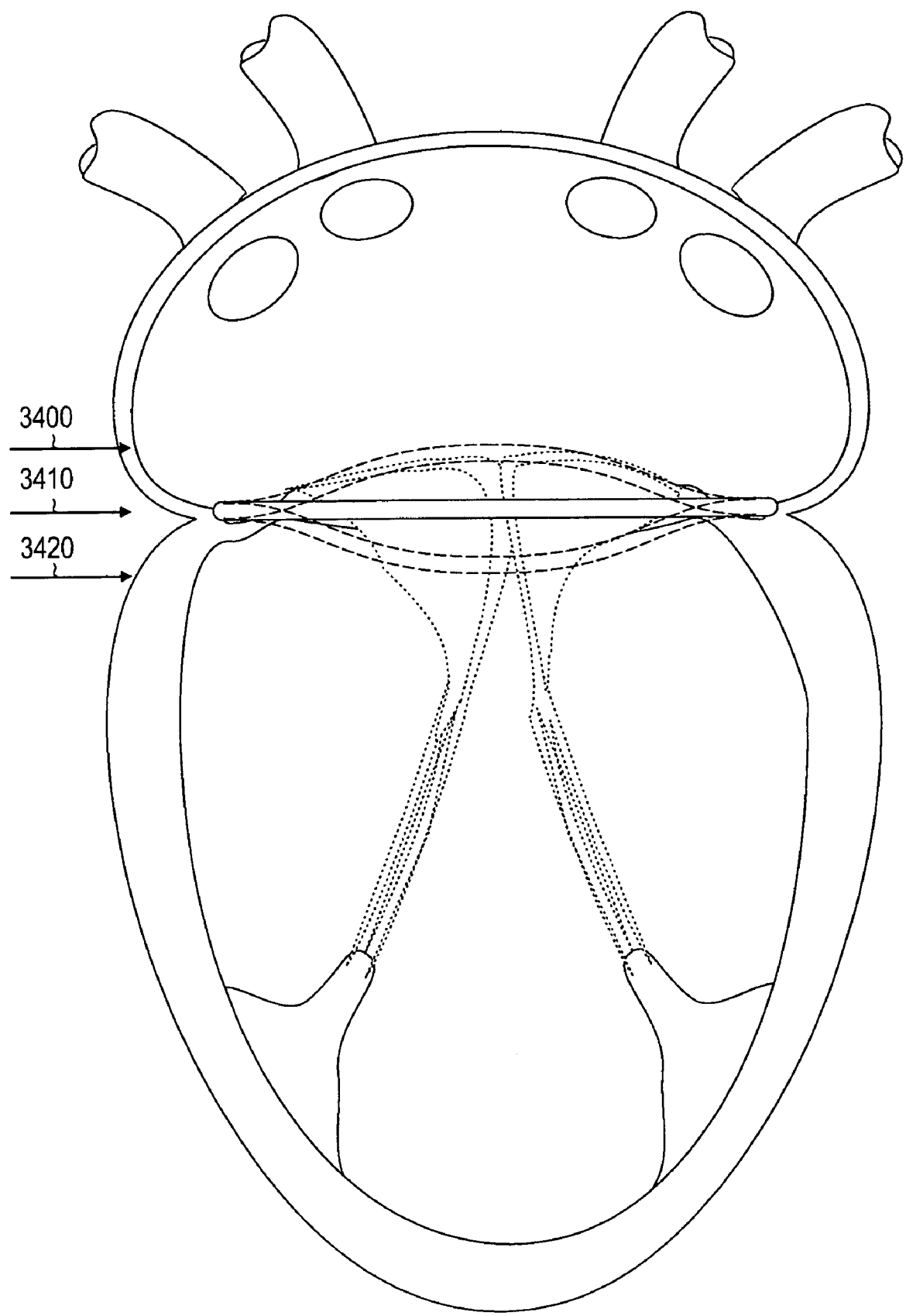
FIG. 34 shows a cutaway view of the left atrium and left ventricle. The arrows on the left side of the figure indicate by way of example three different ways in which an embodiment of the invention, such as a leaflet retainer, neo-leaflet, or neo-annulus, may interact with the mitral valve, or be positioned if replacing a leaflet.

FIG. 34 shows a cutaway view of the left atrium and left ventricle. The arrows on the left side of the figure indicate by way of example three different ways in which an embodiment of the invention, such as a leaflet retainer, neo-leaflet, or neo-annulus, may interact with the mitral valve, or be positioned if replacing a leaflet. In other words, an embodiment of the invention may lie in a plane formed by the annulus of the mitral valve as indicated by the middle arrow 3410. Also, an embodiment of the invention may lie either above or below the plane of the annulus, as indicated by the top 3400 and bottom 3420 arrows, respectively. In addition, FIG. 34 could also be used to illustrate potential movements when these components of the invention are configured as a spring bridge that spans the mitral annulus and actively moves with the valve leaflet(s). A spring bridge may be configured so that it is biased in the open valve position, and is forced shut by increasing pressure within the ventricle. Alternatively, the spring bridge may not be biased open or closed, but simply move in response to pressure differentials. Also, the spring bridge may be biased in the closed position.

Figure 35:
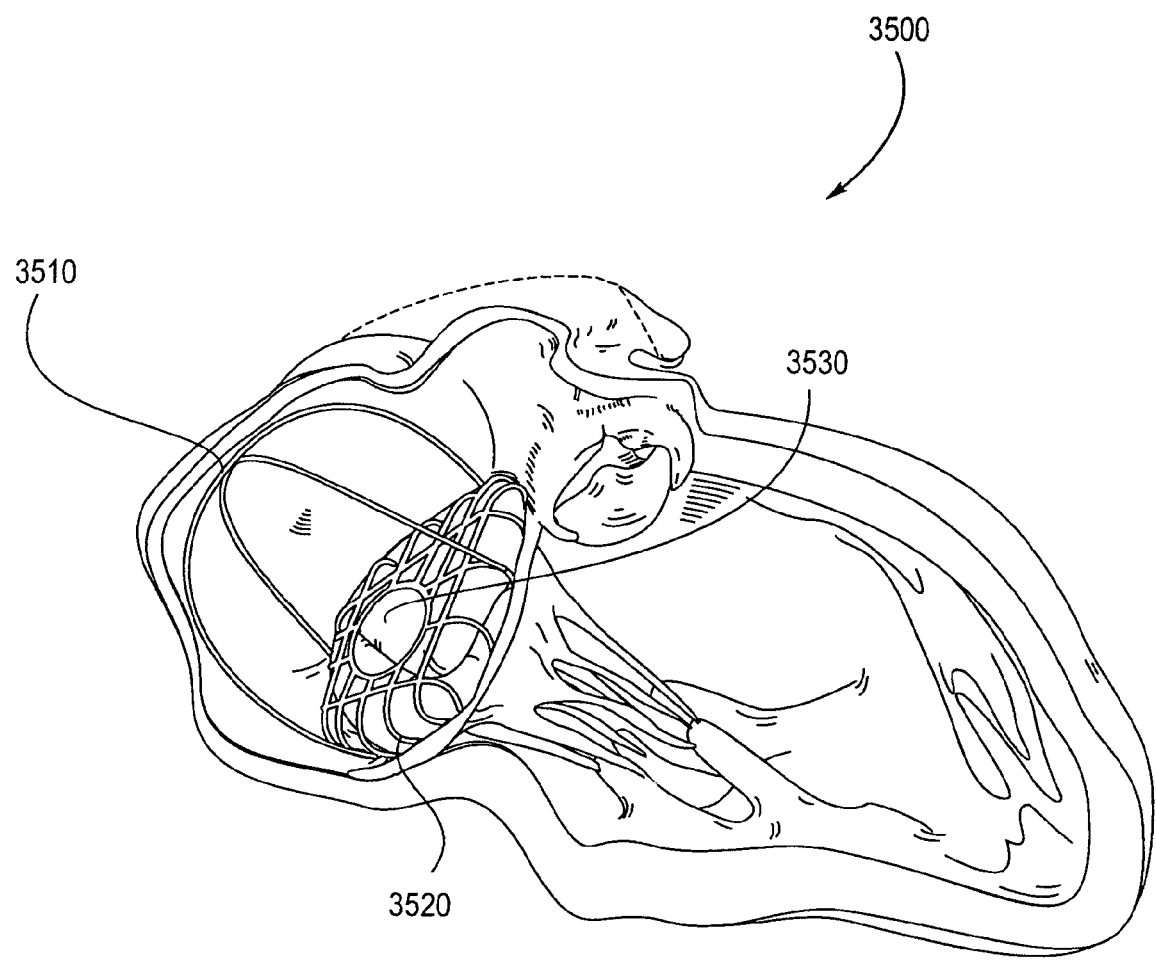
FIG. 35 shows a perspective view of mesh leaflet with buttressing 3500.

FIG. 35 shows a perspective view of mesh leaflet with buttressing 3500. The embodiment is comprised of a framework 3510 and leaflet retainer 3520. The interior region of the valve orifice 3530 of this embodiment is left open to facilitate the flow of blood between the heart's chambers. The leaflet retainer 3520 prevents native leaflets from being blown into the atrium upon ventricular contraction. The framework 3510 transmits mural pressures to the leaflet retainer, encouraging the leaflet retainer to remain positioned over the native leaflets.

Figure 36:
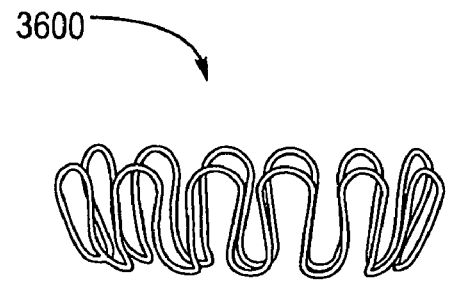
FIG. 36 shows a side view of a corona configuration 3600 of the invention.

FIG. 36 shows a side view of a corona configuration 3600 of the invention. This embodiment may be used as a framework, to which a leaflet retainer or other valve enhancing device could be attached or coupled to.

Figure 37:
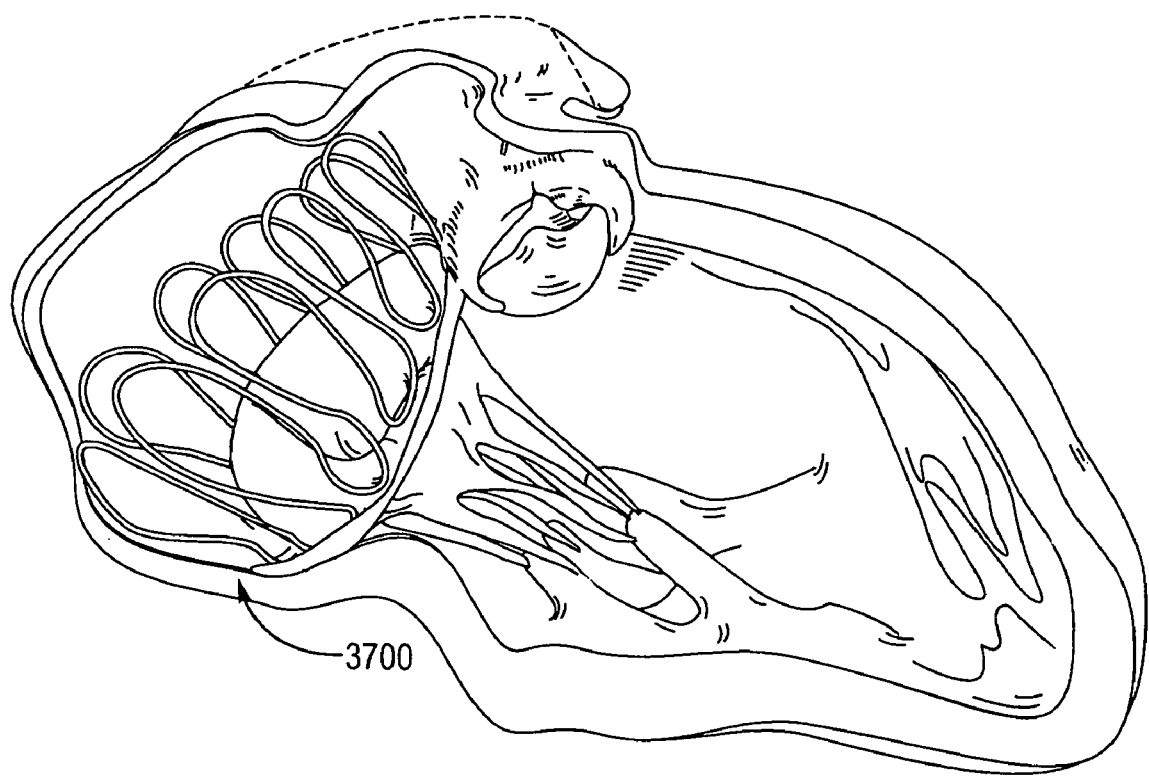
FIG. 37 shows a perspective view of a corona configuration 3700 of the invention in situ within a patient's left atrium.

FIG. 37 shows a perspective view of a corona configuration 3700 of the invention in situ within a patient's left atrium.

Figure 38:
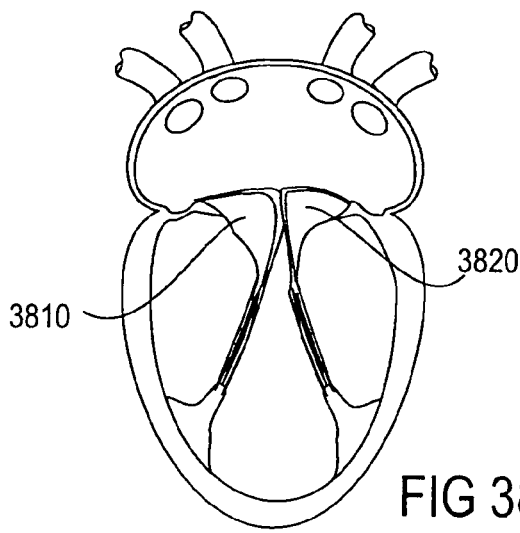
FIG. 38 shows a cutaway view of a heart, having both native leaflets, 3810 and 3820, intact.

FIG. 38 shows a cutaway view of a heart, having both native leaflets, 3810 and 3820, intact.

Figure 39:
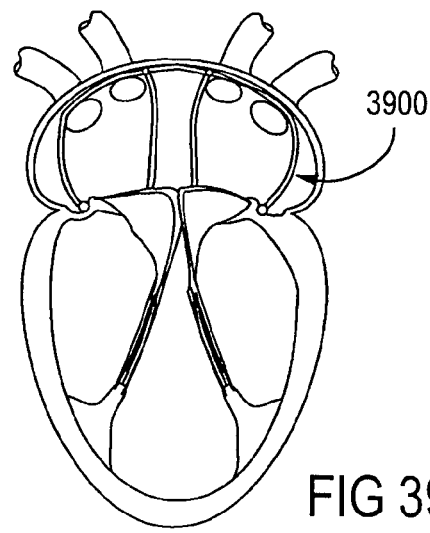
FIG. 39 shows a cutaway view of a heart with one embodiment of the invention 3900.

FIG. 39 shows a cutaway view of a heart with one embodiment of the invention 3900.

Figure 40:
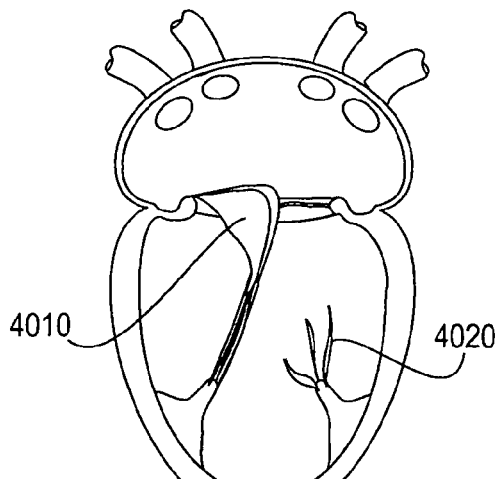
FIG. 40 shows a cutaway view of a heart with one intact mitral valve leaflet 4010, and one mitral valve leaflet excised, or missing.

FIG. 40 shows a cutaway view of a heart with one intact mitral valve leaflet 4010, and one mitral valve leaflet excised, or missing. The chords 4020 of the removed leaflet are shown disconnected.

Figure 41:
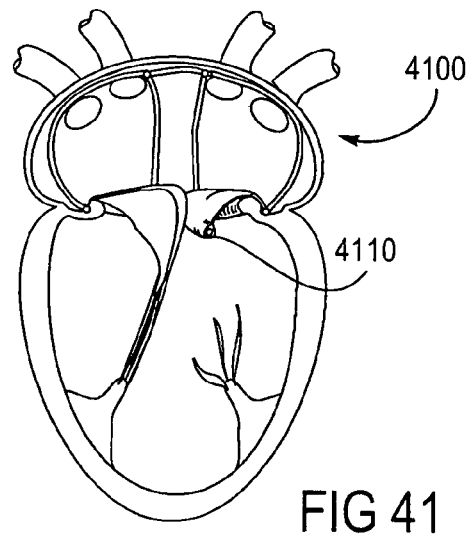
FIG. 41 shows a cutaway view of a heart with one embodiment of the invention 4100. In addition, the shown embodiment has one neo-leaflet 4110.

FIG. 41 shows a cutaway view of a heart with one embodiment of the invention 4100. In addition, the shown embodiment has one neo-leaflet 4110. This neo-leaflet 4110 may be rigid, semi-rigid, or flexible.

Figure 42:
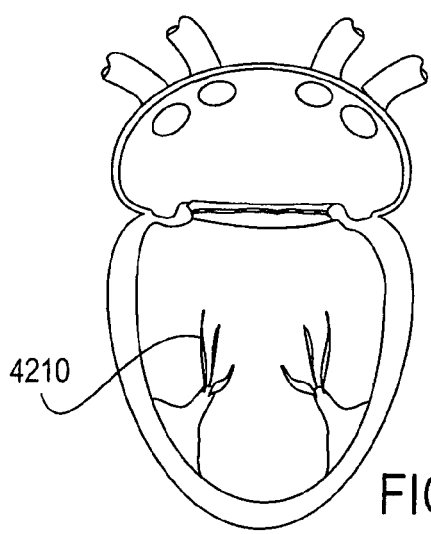
FIG. 42 shows a cutaway view of a heart with both mitral valve leaflets removed.

FIG. 42 shows a cutaway view of a heart with both mitral valve leaflets removed. The chords 4210 are shown disconnected.

Figure 43:
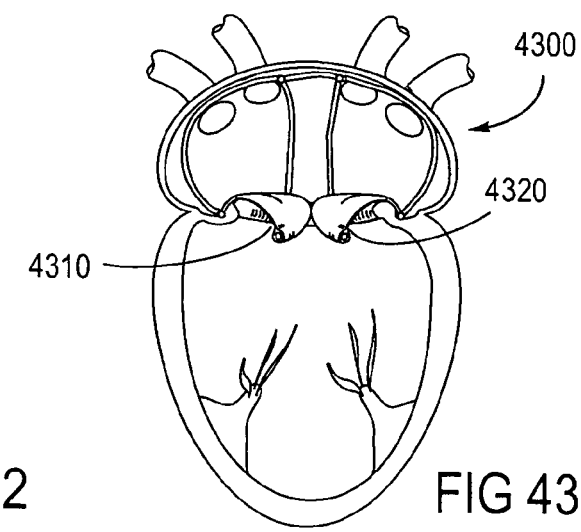
FIG. 43 shows a cutaway view of a heart with one embodiment of the invention 4300 having two neo-leaflets.

FIG. 43 shows a cutaway view of a heart with one embodiment of the invention 4300 having two neo-leaflets.

These devices may be delivered to the heart via open heart surgery, through the chest, or through a remote blood vessel. Examples of delivery through a remote blood vessel include the use of guidewires and catheters. They can be advanced into the right atrium through the superior or inferior vena cava (transluminally, via a peripheral venous insertion site, such as the femoral or jugular vein), or into the left ventricle through the aorta. The left atrium can be accessed from the right atrium through the septum. Alternatively, the left atrium can be accessed from the left ventricle through the mitral valve using a transluminal procedure gaining access via a peripheral arterial insertion site, such as the femoral artery. Echo techniques are used to determine whether a patient is experiencing regurgitation, and various imaging techniques can be used to position the device.

The devices shown may be anchored within the left atrium using barbs, staples, adhesives, magnets, etc. In addition, the devices may be coated with various materials to either promote (Dacron) or inhibit (heparin) tissue growth around the devices, to prevent thrombosis, or coated with other desired materials to encourage other desirable characteristics. Anchoring can also be done on the opposite (ventricular) side of the valve.

While the present invention has been described herein with respect to the exemplary embodiments and the best mode for practicing the invention it will become apparent to one of ordinary skill in the art that many modifications, improvements and sub combinations of the various embodiments, adaptations and variations can be made to the invention without departing from the spirit and scope thereof.

We claim:

1. A method comprising
providing a heart implant sized and configured to be positioned in a left atrium above the plane of a native mitral heart valve annulus having leaflets, the implant including a portion sized and configured for engagement with a wall of the left atrium above the plane of the native mitral valve annulus to interact with movement of the leaflets of the mitral heart valve to affect mitral heart valve function, establishing an intravascular access path that extends from a right atrium through a septum and into a left atrium, deploying the implant through the intravascular path into the left atrium, and positioning the implant in the left atrium with the portion engaging a wall of the left atrium above the plane of the native mitral valve annulus such that the portion interacts with movement of the leaflets of the mitral heart valve to affect mitral heart valve function.

2. A method according to claim 1 wherein the implant is positioned so that the portion spans the left atrium.

3. A method according to claim 1 wherein the implant is positioned so that the portion changes the shape of the native mitral heart valve annulus.

4. A method according to claim 1 wherein the heart implant comprises, at least in part, nitinol, dacron, polytetrafluoroethylene, silicon, polyurethane, human pericardium, or animal pericardium.

5. A method according to claim 1 wherein the heart implant comprises, at least in part, a super elastic material.

* * * * *